(12) United States Patent
Hulvershorn et al.

(10) Patent No.: US 11,896,788 B2
(45) Date of Patent: Feb. 13, 2024

(54) NEEDLE SAFETY CLIP, SYSTEMS AND METHODS

(71) Applicant: Medline Industries, LP, Northfield, IL (US)

(72) Inventors: Justin Hulvershorn, Seattle, WA (US); Karl Schmidt, Seattle, WA (US); Matthew Lovell, Seattle, WA (US)

(73) Assignee: Medline Industries, LP, Northfield, IL (US)

( * ) Notice: Subject to any disclaimer, the term of this patent is extended or adjusted under 35 U.S.C. 154(b) by 125 days.

(21) Appl. No.: 16/307,291

(22) PCT Filed: Jun. 6, 2017

(86) PCT No.: PCT/US2017/036103
§ 371 (c)(1),
(2) Date: Dec. 5, 2018

(87) PCT Pub. No.: WO2017/214110
PCT Pub. Date: Dec. 14, 2017

(65) Prior Publication Data
US 2019/0134356 A1    May 9, 2019

Related U.S. Application Data

(60) Provisional application No. 62/459,838, filed on Feb. 16, 2017, provisional application No. 62/346,210, filed on Jun. 6, 2016.

(51) Int. Cl.
*A61M 25/06* (2006.01)
*A61M 5/32* (2006.01)
*A61M 25/09* (2006.01)

(52) U.S. Cl.
CPC .......... *A61M 25/0631* (2013.01); *A61M 5/32* (2013.01); *A61M 5/3273* (2013.01);
(Continued)

(58) Field of Classification Search
CPC .......... A61M 25/0612; A61M 25/0618; A61M 25/0625; A61M 25/0631; A61M 5/32;
(Continued)

(56) References Cited

U.S. PATENT DOCUMENTS 4,952,207 A    8/1990   Lemieux
5,053,017 A    10/1991  Chamuel
(Continued)

FOREIGN PATENT DOCUMENTS

WO    2016178974    11/2016

OTHER PUBLICATIONS

International Preliminary Report on Patentability for International Application No. PCT/US2017/036103 dated Dec. 11, 2018.
(Continued)

*Primary Examiner* — Emily L Schmidt
*Assistant Examiner* — Alexandra Lalonde
(74) *Attorney, Agent, or Firm* — Fitch, Even, Tabin & Flannery LLP

(57) ABSTRACT

A needle safety clip including means to cover the end of a needle, e.g., after use, and allowing for another medical instrument, e.g., a guidewire or a catheter to extend from the clip with the needle-sharp end secured in the clip. A distal end section of the safety clip includes a slot to receive the guidewire therethrough in a safety position while blocking the needle from moving distally past the distal end section.

13 Claims, 20 Drawing Sheets

(52) U.S. Cl.
CPC .. *A61M 25/0618* (2013.01); *A61M 25/09041* (2013.01); *A61M 25/09* (2013.01)

(58) Field of Classification Search
CPC .............. A61M 5/3273; A61M 5/3202; A61M 5/3205; A61M 5/321; A61M 25/09; A61M 25/09041; A61M 25/0637; A61M 25/0643; A61M 25/0606; A61M 2005/325; A61M 2005/3249; A61M 5/3275; A61M 5/3257; A61M 25/06; A61M 2005/3247
See application file for complete search history.

(56) References Cited

U.S. PATENT DOCUMENTS

| | | | |
|---|---|---|---|
| 5,215,528 A * | 6/1993 | Purdy | A61M 25/0618 604/164.08 |
| 5,558,651 A * | 9/1996 | Crawford | A61M 25/0618 604/110 |
| 5,662,610 A * | 9/1997 | Sircom | A61M 5/3243 604/110 |
| 5,738,665 A * | 4/1998 | Caizza | A61M 5/3275 604/192 |
| 6,280,419 B1 * | 8/2001 | Vojtasek | A61M 25/0618 604/192 |
| 8,273,056 B2 | 9/2012 | Kuracina | |
| 2004/0162526 A1 * | 8/2004 | Vaillancourt | A61M 5/3273 604/192 |
| 2007/0073222 A1 * | 3/2007 | Lilley, Jr. | A61M 25/0618 604/110 |
| 2008/0249480 A1 | 10/2008 | Riesenberger | |
| 2011/0060294 A1 * | 3/2011 | Baid | A61M 25/0618 604/263 |
| 2012/0046620 A1 * | 2/2012 | Woehr | A61M 25/0097 604/263 |
| 2015/0051584 A1 | 2/2015 | Korkuch | |

OTHER PUBLICATIONS

International Search Report for International Application No. PCT/US2017/036103 dated Aug. 24, 2017.

* cited by examiner

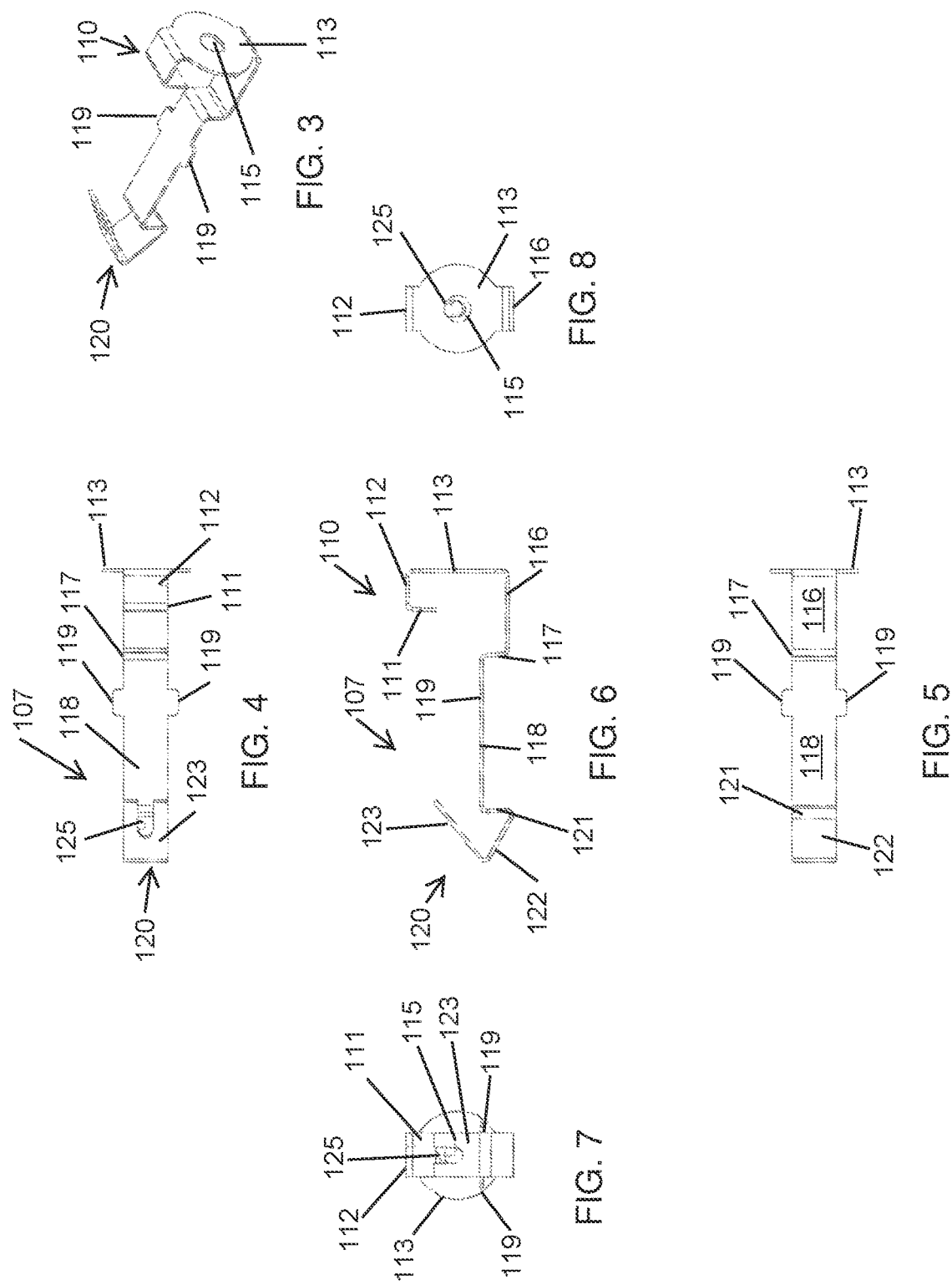

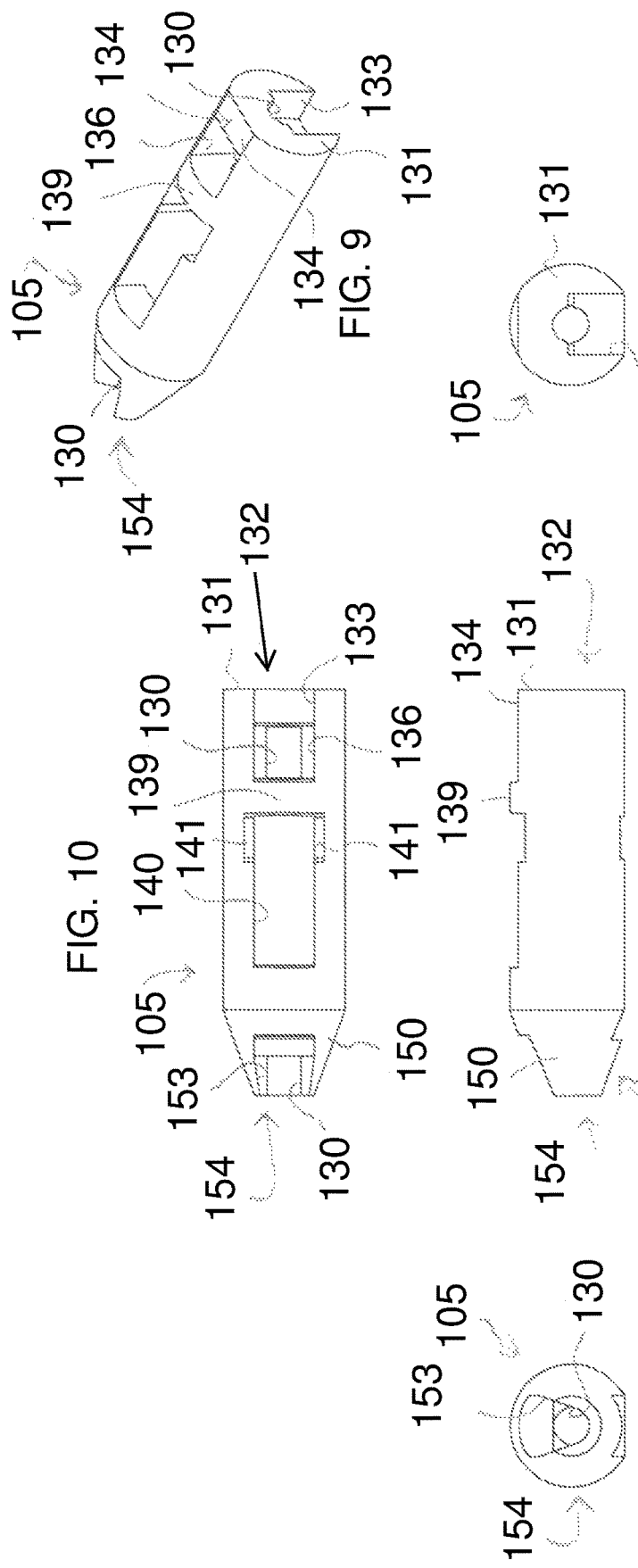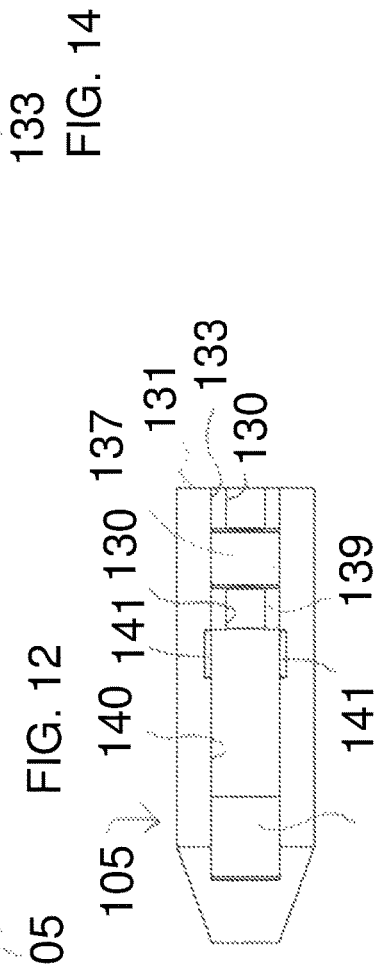

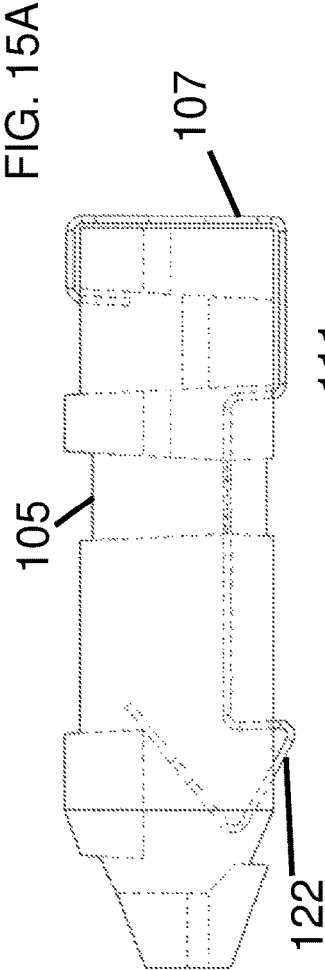
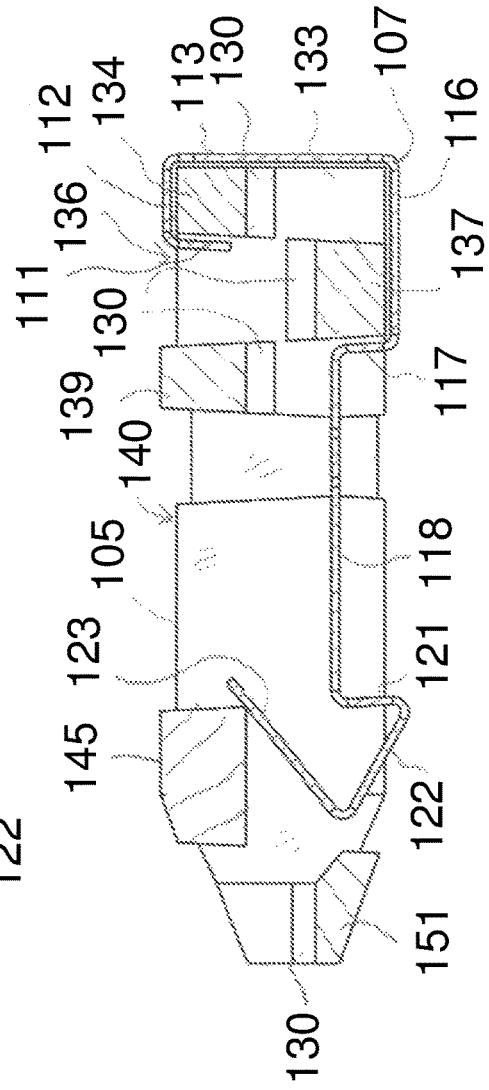
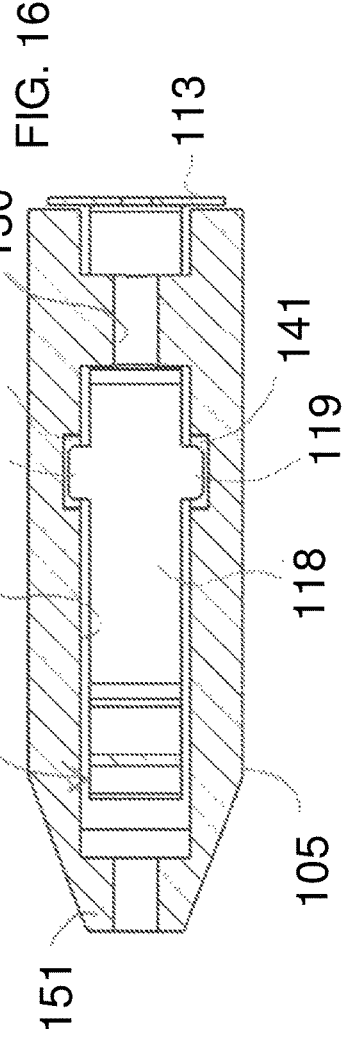

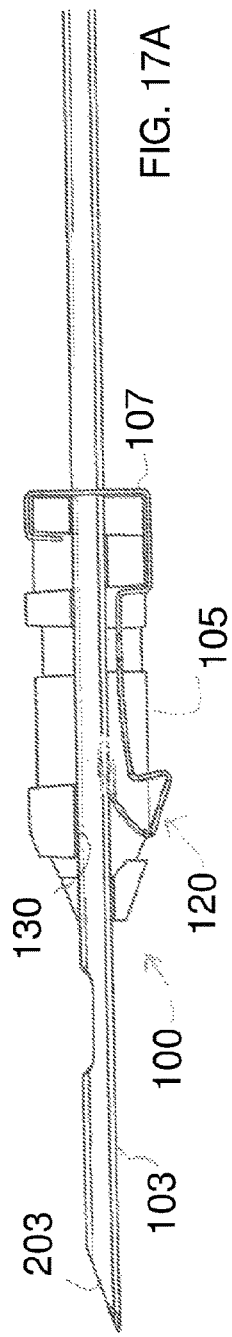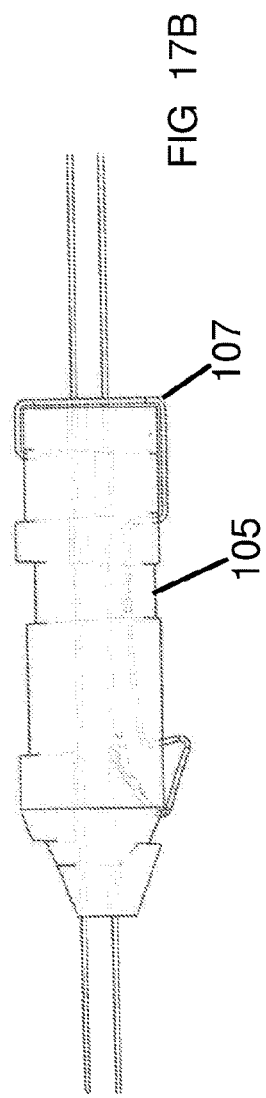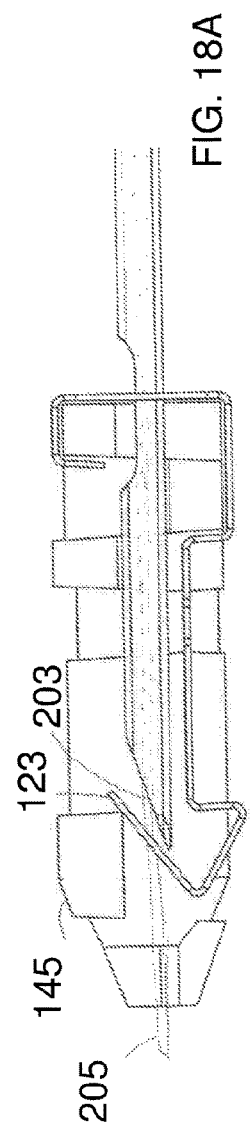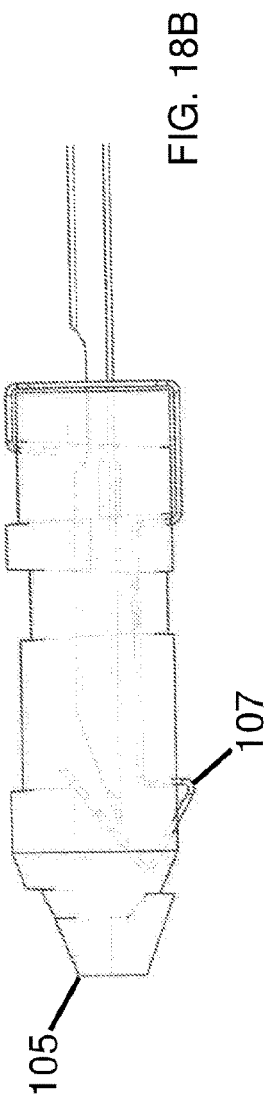

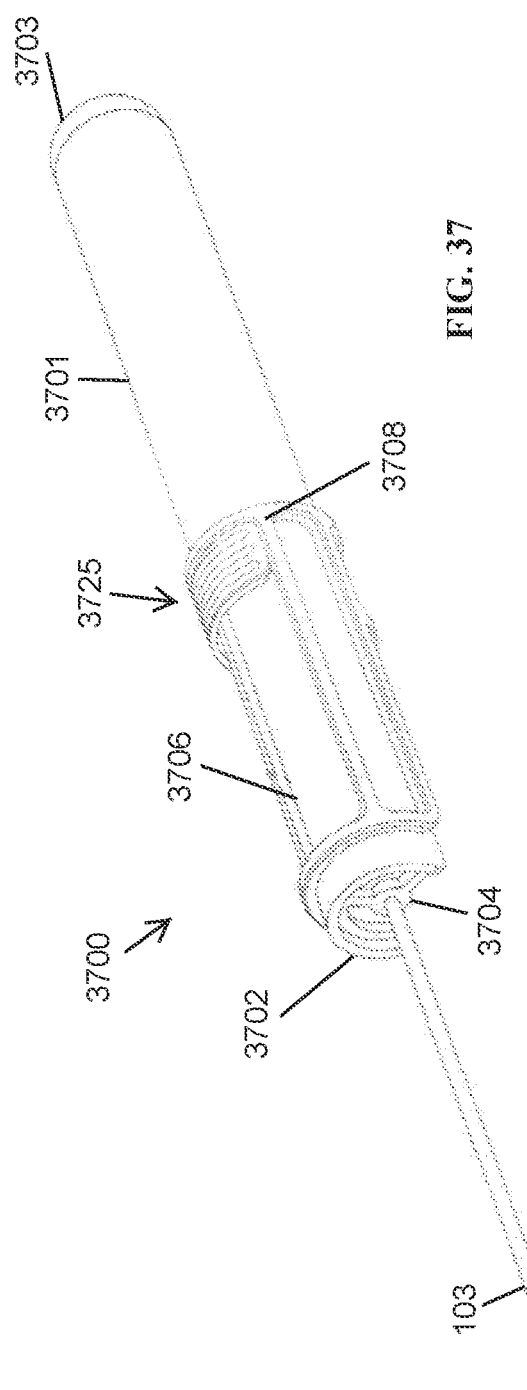
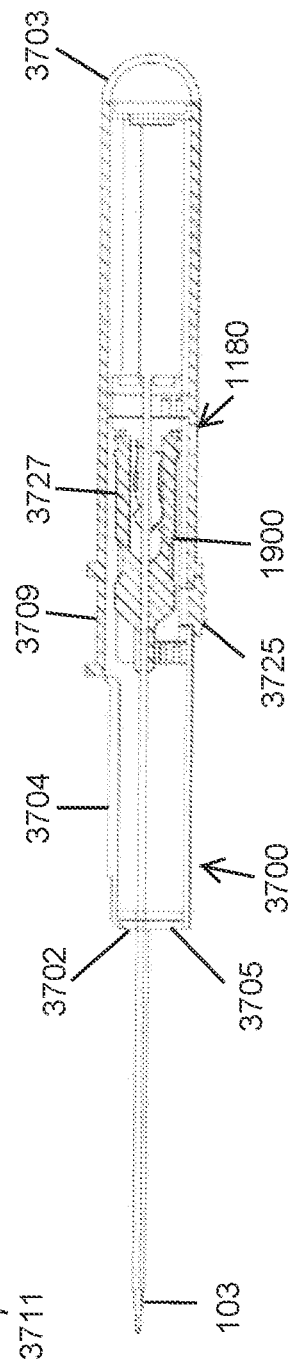

NEEDLE SAFETY CLIP, SYSTEMS AND METHODS

CROSS-REFERENCE TO RELATED APPLICATIONS

This application is the U.S. national phase of PCT Appln. No. PCT/US2017/036103 filed Jun. 6, 2017 which claims the benefit of U.S. provisional application Ser. No. 62/346,210 filed Jun. 6, 2016 and U.S. provisional application Ser. No. 62/459,838 filed Feb. 16, 2017, the disclosures of which are hereby incorporated in their entirety by reference herein.

TECHNICAL FIELD

Aspects of the present disclosure provide for structures, systems and methods for needle safety clips.

BACKGROUND

Medical care of people and animals requires the use the sharp instruments, e.g., needles. After use, a needle must be handled carefully to prevent needle stick injuries. Needle safety devices are used to cover the needle tip after use. The needle safety devices can be passive or active. A passive needle safety device does not require user activation, i.e., the safety device is automatically deployed without user intervention. An active needle safety device requires user invention to deploy and cover the needle tip.

SUMMARY

A needle safety clip is described that secures a needle-sharp end after use while allowing a medical instrument, e.g., a guidewire to extend proximally toward a patient from the needle and the safety clip. The safety clip can have an arm that is biased to a closed position to secure the needle when the needle is retracted distally past the arm free end. In some examples, the needle safety clip operates passively. The arm includes a slot to allow a guidewire to extend past the end of the safety clip with the needle-sharp end being secured in the needle clip.

An example of a needle safety clip can include a proximal wall including an aperture sized to receive a needle therethrough. The arm extends distally from the proximal wall and includes the slot to receive the guidewire therethrough in a safety position. In an example, there is only a single arm within a housing. The housing may prevent access to the needle-sharp end and prevents the needle from being worked past the free end after the needle is retracted.

A needle safety clip assembly is described with a needle safety clip to cover an sharp end of a needle while allowing a guide wire to extend through the needle safety clip. In an example, the needle safety clip includes a housing having a proximal end, a distal end, and an aperture and a needle safety clip extending around the proximal end to fix the clip on the housing, the clip including a first section extending into the aperture and a second section distal the first section, which at a use position is pressed against a needle and at a safety position with the distal section securing a sharp end within the housing. In an example embodiment, the second section includes a slot to receive a guidewire therethrough in a safety position.

In an example embodiment, the slot is open at a free edge of second section of the needle safety clip.

In an example embodiment, the second section flexes to allow a needle to pass through the housing and with the needle retracted past a distal end of the second section.

In an example embodiment, the first section wraps around a proximal end of the housing to secure the needle safety clip to the housing.

In an example embodiment, the housing encloses sides of the aperture in both the use position and the safety position and the section second section encloses a sharp end of the needle in the safety position.

In an example embodiment, the second section includes a first subsection extending outwardly of the housing to engage a catheter hub to prevent the needle safety clip and the housing from being moved distally of the catheter hub.

In an example embodiment, the needle safety clip flexes adjacent the first subsection of the second section.

In an example embodiment, the needles safety clip flexes in the second section.

In an example embodiment, the first section includes a proximal wall that is spaced from the second section a distance greater than a distance from a sharp end of the needle and a stop protuberance on a shaft of the needle adjacent the proximal wall such that the sharp end of the needle cannot travel proximally of the proximal wall or distally of the second section.

A medical device using the above needle safety structure or assembly. An example medical device can include a catheter hub having a hollow interior, a needle safety clip assembly mounted completely within the hollow interior of the catherer hub, and a needle extending through the needle safety clip assembly and the catheter hub in a use position and retracted into the needle safety clip assembly in the safety position. In an example embodiment, the needle safety clip assembly includes a clip housing having a proximal end, a distal end, and an aperture, a needle safety clip extending around the proximal end to fix the clip on the clip housing, the clip including a first section extending into the aperture and a second section distal the first section, which at a use position is pressed against a needle and at a safety position with the distal section securing a sharp end within the housing. In an example embodiment, the second section includes a slot to receive a guidewire therethrough in a safety position.

In an example embodiment, the needle clip assembly has a length less than a length of the interior of the catheter.

In an example embodiment, a guide wire extending through the needle in both the use position and the safety position.

In an example embodiment, the needle safety clip and the needle are retractable proximally to remove the needle safety clip and the enclosed sharp end of the needle from the catheter hub with the guide wire remaining in the catheter hub and a body of a patient.

A needle safety clip is described that secures a needle-sharp end after use while allowing a medical instrument, e.g., a guidewire to extend proximally toward a patient from the needle and the safety clip. The safety clip can have two arms that are biased to a closed position to secure the needle when the needle is retracted distally past the ends of the arms. The arms may include sidewalls to help secure the needle end. The arms need not cross or intersect in some examples. In some examples, the needle safety clip operates passively.

An example of a needle safety clip can include a proximal wall including an aperture sized to receive a needle therethrough, a first arm extending distally from the proximal wall and including a first slot to receive the guidewire therethrough in a safety position, and a second arm extending distally from the proximal wall and including a second slot to receive the guidewire therethrough in the safety position. The first arm and the second arm are open in a use position with a needle extending past the first arm and the second arm such the needle-sharp end may engage a patient's body.

In an example, at least one of the first arm and the second arm is biased to move from the use position to the safety position with the needle retracted past the second arm with at least part of the first slot and the second slot being aligned to allow the guide wire to extend therethrough with the needle in the safety position.

In an example, the second arm includes at least two side walls outwardly of the second slot. In operation, the side walls may assist in securing the needle-sharp end.

In an example, the second arm is cantilevered from the proximal wall and includes a top wall extending proximally from a free end of the second arm to prevent the needle from passing above the second arm in the safety position. This may assist in securing the needle-sharp end in the safety clip.

In an example, the second arm includes a main body wider than a main body of the first arm.

In an example, the first arm main body is cantilevered from the proximal wall and includes two side walls extending toward the second arm main body. The side walls may assist in securing the needle-sharp end in the safety clip.

In an example, the two side walls of the first arm main body are essentially planar and extend between the distal end of the first arm and the proximal end of the first arm.

In an example, the first arm includes a first finger and a second finger that form the slot, wherein both the first finger and the second finger include a sidewall between which the needle extends.

In an example, the first arm main body and the second arm main body do not intersect.

In an example, the proximal wall is planar. The proximal wall aperture has a dimension greater than a main needle part and smaller than a profile change in the needle to prevent the needle from exiting proximally past the proximal wall.

In an example, the first arm includes a first dimension adjacent the proximal wall and a second dimension smaller than the first dimension distally from the first dimension, and a third dimension greater than the second dimension distally from the second dimension. In an example, the second arm includes a fourth dimension adjacent the proximal wall and a fifth dimension smaller than the fourth dimension distally from the fourth dimension.

In an example, the first arm main body includes two side walls at the second dimension extending toward the fifth dimension of the second arm. The two side walls may assist in securing the needle in the safety clip.

In an example, the two side walls of the first arm main body are essentially planar and extend between the distal end of the first arm and the proximal end of the first arm.

In an example, the first arm includes a first finger and a second finger that form the first slot at the third dimension, wherein both the first finger and the second finger include a sidewall between which the needle extends. The finger sidewalls may assist in securing the needle-sharp end in the safety clip.

In an example, the proximal wall, the first arm and the second arm are formed from a single body with the first arm and the second arm being cantilevered from edges of the proximal wall. The first arm and the second arm are both biased from the use position to the safety position. At least a portion of the first arm and the second arm are biased to overlap the other at the free ends in the safety position.

Another needle safety clip embodiment includes a proximal wall including a first aperture sized to receive a needle therethrough, a first arm extending distally from the proximal wall and including a first slot at a first free end of the first arm, a second arm extending distally from the proximal wall and including a second slot at a second free end of the second arm. In an example, the first arm can be held in an open position with the needle extending past the first arm. The first arm can be urged to a closed position with the needle withdrawn proximally of the first free end of the first arm. In an example, the second arm is held in the open position with the needle extending past the second arm. The second arm can be urged to the closed position with the needle withdrawn proximally of the second free end of the second arm. In an example, the second arm is biased to move to a safety position with the needle retracted past the second arm with at least part of the second slot, the first slot and the proximal wall aperture being aligned to allow a further medical device to extend therethrough with the needle in the safety position.

In an example, the second arm includes at least two side walls outwardly of the second slot.

In an example, the second arm is cantilevered from the proximal wall and includes a top wall extending proximally from a free end of the second arm to prevent the needle from passing above the second arm in the safety position.

In an example, the second arm includes a main body wider than a main body of the first arm.

In an example, the first arm main body is cantilevered from the proximal and includes two side walls extending toward the second arm main body.

In an example, the two side walls of the first arm main body are essentially planar and extend between the distal end of the first arm and the proximal end of the first arm.

In an example, the first arm includes a first finger and a second finger that form the slot.

In an example, both the first finger and the second finger include a sidewall between which the needle extends.

In an example, the proximal wall is spaced from a closest one of the first free end and the second free end a distance greater than a distance from a sharp end of the needle and a stop on a shaft of the needle adjacent the proximal wall such that the sharp end of the needle cannot travel proximally of the proximal wall or distally of the first free end or the second free end.

BRIEF DESCRIPTION OF THE DRAWINGS

The embodiments of the present disclosure are pointed out with particularity in the appended claims. However, other features of the various embodiments will become more apparent and will be best understood by referring to the following detailed description in conjunction with the accompany figures (FIGS.) in which:

FIG. 3 shows a perspective view of a needle safety clip according to an embodiment.

FIG. 4 shows a top view of a needle safety clip according to an embodiment.

FIG. 5 shows a bottom view of a needle safety clip according to an embodiment.

FIG. 6 shows an elevational view of a needle safety clip according to an embodiment.

FIG. 7 shows a distal end view of a needle safety clip according to an embodiment.

FIG. 8 shows a proximal end view of a needle safety clip according to an embodiment.

FIG. 9 shows a perspective view of a clip housing according to an embodiment.

FIG. 10 shows a top view of a clip housing according to an embodiment.

FIG. 11 shows a bottom view of a clip housing according to an embodiment.

FIG. 12 shows an elevational view of a clip housing according to an embodiment.

FIG. 13 shows a distal end view of a clip housing according to an embodiment.

FIG. 14 shows a proximal end view of a clip housing according to an embodiment.

FIG. 15A shows a side view of the needle safety clip in a clip housing according to an embodiment.

FIG. 15B shows a vertical cross section view of a needle safety clip in a clip housing according to an embodiment.

FIG. 16 shows a horizontal cross section view of a needle safety clip in a clip housing according to an embodiment.

FIG. 17A shows a vertical cross section view of a medical device assembly, in a use position, according to an embodiment.

FIG. 17B shows a side view of the medical device assembly of FIG. 17A.

FIG. 18A shows a vertical cross section view of a medical device assembly, in a closed position, according to an embodiment.

FIG. 18B shows a side view of the medical device assembly of FIG. 18A.

FIG. 37 shows a perspective view of a medical device with a needle safety clip according to an embodiment.

FIG. 38 shows a cross sectional view of the FIG. 37 medical device.

DETAILED DESCRIPTION

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

A medical device is described that provides for both securing the sharp end and allowing for additional medical equipment that may be associated with a needle, e.g., a guidewire, a catheter, and the like, to continue to engage a patient when the needle is removed and secured by the needle safety clip. Medical personnel must use caution after using a needle in a procedure as the sharp end may not be secured. A secured needle-sharp end is one that is covered to prevent accidental sticks or reuse of the needle. The presently described examples of a needle safety clip provide for a path through the needle safety clip for the passage of additional medical equipment with the needle is secured in the clip.

Figure 1:
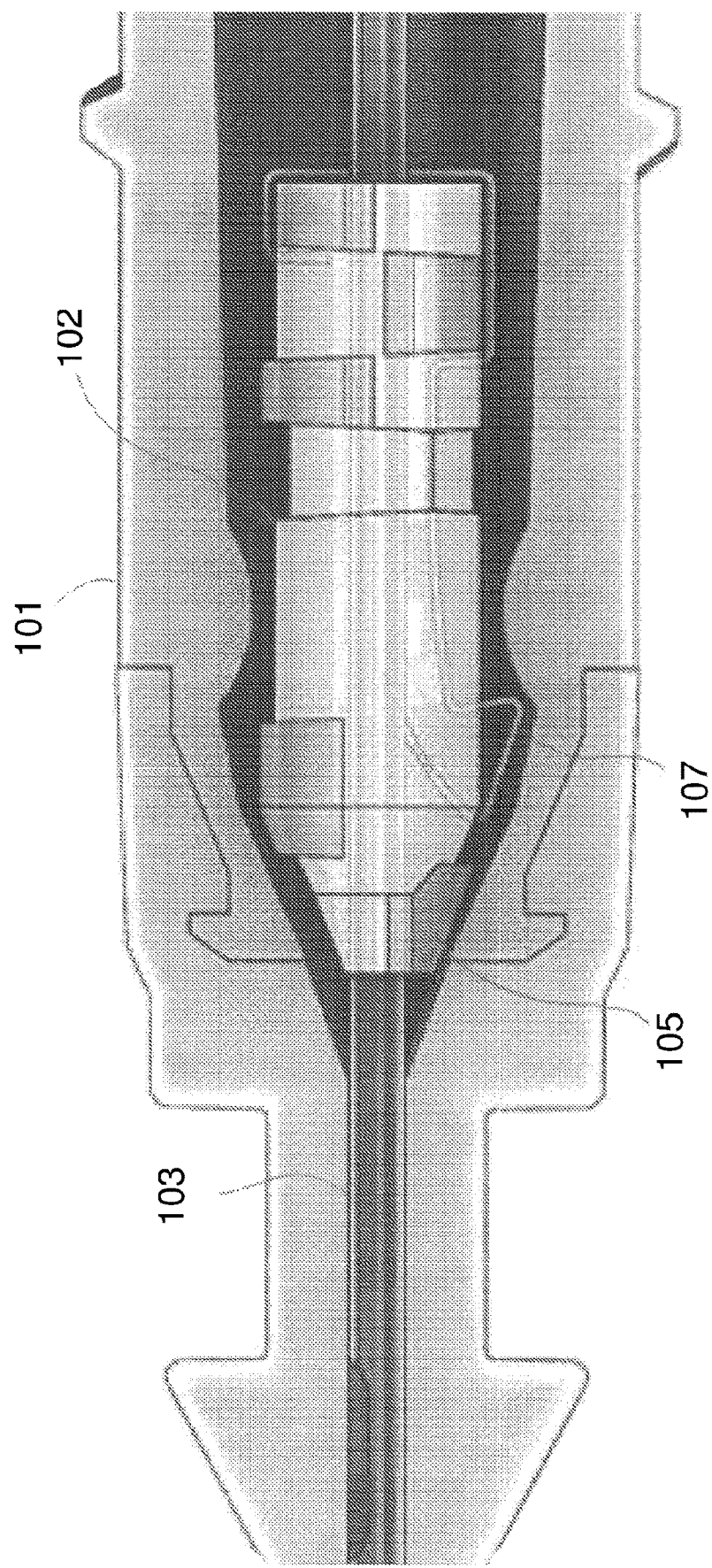
FIG. 1 shows a view of a medical device with a needle safety clip according to an embodiment.
Figure 2:
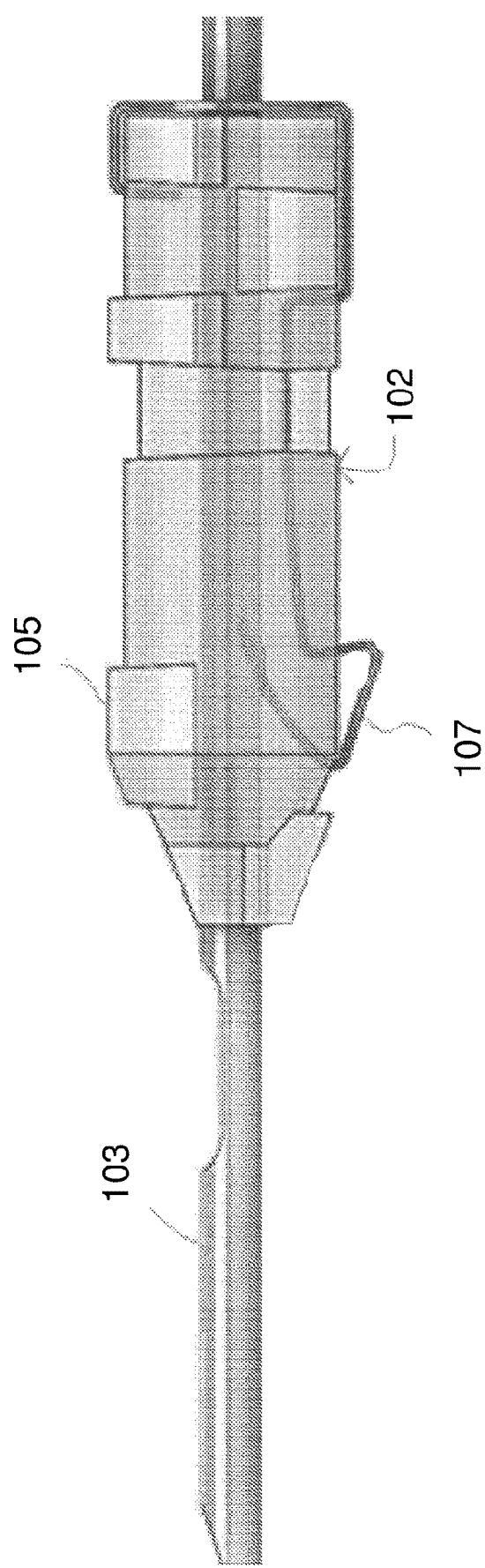
FIG. 2 shows a view of a medical device with a needle safety clip according to an embodiment.

FIG. 1 shows a medical device 100 with a catheter hub 101 and a needle safety assembly 102 with in the catheter hub 101. A needle 103 extends through the catheter hub 101 and the needle safety assembly 102. A guide wire may extend through the needle 103. The needle safety assembly 102 includes a housing 105 and a safety clip 107 attached to the housing with a portion thereof within the housing 105. In operation, the needle 103 extends distally from the housing 105 and past the safety clip 107, and out of a medical device, e.g., a catheter or other insertion device, to engage a patient's body, e.g., insertion into a patient's vasculature. The needle safety clip 107 is shown in the use position with a needle 103 extending through the needle safety clip 107 and housing 105. The needle can freely travel proximally to retract the needle 103 such that the sharp end of the needle retracts into housing 105 past a free end of the safety clip 107.

FIGS. 3-8 shows various views of the safety clip 107. FIG. 3 shows a rear perspective view. FIG. 4 shows a top view of the safety clip 107. FIG. 5 shows a bottom view of the safety clip 107. FIG. 6 shows a side elevational view of the safety clip 107. FIG. 7 shows a front view of the safety clip 107. FIG. 8 shows a rear view of the safety clip 107. The safety clip 107 includes a proximal end 110 that fixes to the housing. The safety clip 107 includes a distal end 120 that is moveable to secure the sharp end of the needle 107 in a closed position and deflects in a use position to allow the needle to be used in a medical procedure. The proximal end 110 is included in a first section that includes a first subsection 111 that extends downwardly toward the longitudinal dimension to the safety clip 107. A second subsection 112 is connected between the first subsection 111 and a rear wall 113. The first and second subsections 111, 112 are rectangular solids. The first and second subsections 111, 112 can have the same width. The second subsection 112 is at an angle to the first subsection 111, e.g., orthogonal to the first subsection 111. The rear wall 113 is not rectangular, e.g., a round, oval or circular shape. The rear wall 113 can have a lateral dimension that is greater than the width of the first and second subsections 111, 112. The rear wall 113 includes an aperture 115 centrally positioned therein. The aperture 115 is positioned downwardly of the free end of the first subsection 111. The aperture 115 is sized to receive a needle there through. The aperture 115 is sized to allow the needle to slide longitudinally in the aperture 115. In an example embodiment, the aperture 115 is sized to closely match the outer diameter of the needle and when the needle includes a protuberance distal of the rear wall 113, the rear wall stops the needle from moving further proximally with the protuberance stopped inside the needle safety clip and the housing.

The safety clip 107 can be formed from a single body, e.g., a metal, steel, stainless steel, or a rigid polymer. The body of the safety clip 107 can be formed from a generally planar blank and bent into shape with the slot 125 and aperture 115 punched into the body. The body of the safety clip 107 can be formed from a thin wall blank, e.g., a thickness of less than about 0.0035 inch, +/−0.0005 inch. The aperture 115 to receive the needle is centrally positioned in the proximal wall. The center of the aperture 115 can define the longitudinal axis of the safety clip 107, which is also the center longitudinal axis of the assembled medical device 100.

The center portion of the safety clip 107 includes a third subsection 116 extending distally from the rear wall 113. The third subsection 116 can be parallel to the second subsection 112 and orthogonal to the rear wall 113. The third subsection 116 can have the same width as the first and second subsections 111, 112. The third subsection 116 has a longitudinal length greater than the longitudinal length of the second subsection 112. The center portion of the safety clip 107 includes a fourth subsection 117 extending upwardly toward the longitudinal axis. The fourth subsection 117 has a height less than the height of the rear wall 113, and has a height less than half the height of the rear wall. The height of the fourth subsection 117 is less than the distance from the lowest point of the aperture 115.

The center portion of the safety clip 107 includes a fifth subsection 118 extending distally from the fourth subsection 113 to a free end structure of 120 of the safety clip 107. The fifth subsection 118 has a longitudinal length greater than the longitudinal lengths of the second subsection 112 and the third subsection 116. A plurality of wings 119 extend outwardly from sides of the fifth subsection 118. The wings 119 do not extend outwardly of the rear wall 113. In an example, the wings 119 extend outwardly to match the width of the rear wall 113 at a chord of the rear wall aligned with the fifth wall subsection 118. The wings 119 can be formed from the same blank as the fifth subsection 118.

The free end structure 120 is formed to work with the housing to secure the needle-sharp end in the safety position and deflect out of the path of the needle in the use position as will be described in greater detail herein. The free end structure 120 includes a sixth subsection 121 extending downwardly from the distal end of the fifth subsection 118. The sixth subsection 121 is orthogonal to the fifth subsection 118. A seventh subsection 122 extends upwardly from the lower end of the sixth subsection 121. The seventh subsection 122 is non-orthogonal to the sixth subsection 121. In an example, the seventh subsection 122 extends at an angle of about 30.0 degrees, or in a range of about 20.0 degrees to about 40.0 degrees, or in a range of about 25.0 degrees to about 35.0 degrees, +/−1.0 degrees, upwardly relative to the sixth subsection 121. An eighth subsection 123 extends rearwardly (back toward the rear wall 113) from the seventh subsection 122 at an angle of less than 90.0 degrees. The eighth subsection 123 is cantilevered from the seventh subsection 122.

A slot 125 is formed in the eighth subsection 123 extending downwardly from the free edge of the eighth subsection 123. The slot 125 is formed to have dimension less than a smallest dimension of the needle 103. The slot 125 is longitudinally aligned with the aperture 115, in both the safety position (as shown in FIGS. 3-8) and in the use position. In an example embodiment, the slot 125 is aligned with the aperture 115 in the closed, safety position. The slot 125 is laterally offset from the aperture in the use position. The slot 125 is sized such that a medical tool, which can extend through the hollow interior of the needle 103, can extend through the slot 125. The slot 125 has a width that is less than the diameter (or smallest dimension) of the aperture 115. A slot 125 is used such that when the free end structure 120 to allow the medical tool to remain extended through the safety clip 107 with the needle is retracted into the safety position. That is, the free end structure 120 pivots upwardly with the needle 103 behind the free end structure 120 with the medical tool moving into the slot 125.

In an example, the first through eight subsections 111, 112, 116-118, and 121-123 have a same width, absent the wings 119 on the fifth subsection 118. Thus, each of the subsections can have different lengths and the same width.

In operation, the free end structure 120 flexes downwardly to allow a needle to pass over the top of the eighth subsection 123 at its free edge. The safety clip 107 can flex at the joint between the sixth wall subsection 121 and the fifth wall subsection 118. In an example, the safety clip 107 may flex along the length of the fifth subsection 118. In an example, the safety clip 107 may flex at the joint between the eighth wall subsection 123 and the seventh wall subsection 122.

Turning now to the clip housing 103, it is shown in FIGS. 9-14. FIG. 9 shows a rear perspective view of the housing 105. FIG. 10 shows a top view of the housing 105. FIG. 11 shows a bottom view of the housing 105. FIG. 12 shows a side elevational view of the housing 105. FIG. 13 shows a front view of the housing 105. FIG. 14 shows a rear view of the housing 105. The housing 105 is formed from a unitary body, which can be a polymer, a metal or other surgical grade substance. The housing 105 includes a through aperture 130 that extends through the body of the housing from the proximal end 132 to the distal end 154 and is sized to slidably receive a needle therein. The aperture 130 is aligned or coaxial with the safety clip aperture 115 when assembled. The housing 103 includes, at the proximal end 132, a flat rear wall 131. A notch 133 is formed at the proximal end 132 in the rear wall 131 and the bottom of the housing.

A rear web 134 extends above the notch 133 to close the top of the notch 133. The top surface 135 of the web 134 is planar. The bottom surface of the web 134 may include a bottom facing trough that defines a portion of the through aperture 130. A top recess 136 is distal from the rear web 134 with a distal side of the rear web defining the rear surface of the top aperture 134. A bottom web 137 defines the bottom surface of the top recess 136. The top surface of the bottom web 137 may include a trough that is upward facing and defines a portion of the through aperture 130. A further top web 139 is positioned distally of the top recess 136 with a proximal surface of the web 139 forming the distal side of the top recess 136. A downward surface of the web 139 includes a trough to form a portion of the through aperture 130.

A distal top aperture 140 extends into the body of the housing 105 distal of the web 19. When viewed from the top the aperture 140 has a cross shape with the cross member being shorter than the base member, which extends longitudinally. The long member of the aperture 140 extends from the top of the housing to the bottom of the housing. The cross member at the lateral sides does not extend all the way through the housing 105. A shelf 141 is at the bottom of the aperture 140. The shelf 140 operate at stops for the wings 119.

A distal top web 145 is positioned distally of the aperture 140. A proximal surface of the web 145 forms the distal surface of the top aperture 140. The bottom surface of the web 145 forms a stop for the free end structure 120 with the safety clip 107 when it is in the safety position. The volume of the housing 105 beneath the web 145 is open and a distal portion of the aperture.

A distal part 150 of the housing 105 is at the distal end and is generally conical relative to the generally cylindrical distal port of the housing. The housing distal part includes a bottom web 151, which includes an upward facing trough that defines a portion of the through aperture 130. The distal part 150 includes a recess 153 above the web 151.

The webs 134, 137, 139, and 145 extend from one side of the housing to the other. An aperture or recess separates the webs from each other.

FIGS. 15A and 15B show a elevational side view and a vertical cross sectional view of the safety clip assembly, respectively, with the housing 105 and the safety clip 107. The safety clip 107 is mounted onto the housing 105 with the first subsection 111 on the distal side of the rear web 134, the second subsection 112 on the top of the rear web 134, and the rear wall 113 on the proximal face of the rear web 134. The rear wall 113 extends from the rear web 134 to the bottom of the housing 105 with the third subsection 116 extending along the bottom of the housing and partially along the bottom face of the web 137. The fourth subsection 117 extend upwardly into the aperture 140 along the distal face of the web 137. The fifth subsection 118 is recessed inside the aperture 140. The wings 119 extend onto the top of the shelves 141. The wings 119 being on top of the shelves 141 and the subsections 111, 112, and 113 fix the safety clip 107 in the housing. Distally of the wings 119, the body of the safety clip is free to flex downwardly from its safety position that is shown in FIGS. 15 and 16. At least part of the sixth subsection 121 and seventh subsection 122, e.g., at the joint there between, extends below the housing 105. In the use position, the safety clip may flex at the fifth subsection 118 distally of the wings 119 or along the distal subsections 121-123. The eighth subsection 123 is in contact with the web 145 to prevent the distal end of the clip 107 from flexing or pivoting upwardly out of the aperture 140 in the housing 105.

FIG. 16 shows a horizontal cross sectional view of the safety clip assembly with the housing 105 and the safety clip 107. The wings 119 are shown on the selves 141.

FIG. 17 shows a cross section view, absent cross hatching, of the needle safety assembly 102 in the use position with the needle 103 extending through the housing 105 and past the needle safety clip 107. The distal end structure 120 of the safety clip 107 is flexed downwardly to allow the needle 103 to pass through the center aperture 130. The subsection 123 presses against the bottom surface of the needle.

FIG. 18 shows the needle safety assembly 102 in the safety position with the sharp end 203 retracted proximally past the subsection 123. The end structure 120 is pivoted upwardly relative to the use position such that the subsection 123 extends up and over the sharp end 203. The housing 105 defining the through aperture 130 contacts the needle in a plurality of locations such that the needle cannot be pivoted past the subsection 123. A guide wire 205 extends distally past the needle-sharp end 203 and through the slot 125 in the subsection 123.

While not shown in the drawings the needle 103 may include structures to prevent the needle from being retracted through the distal end of the housing 105. In an example, the needle may include a protrusion that is larger than the aperture 115 in the rear wall or part of the through aperture 130. The protrusion would act as a stop when it contacts the housing.

The needle safety assembly can be part of a medical device, e.g., a vascular access catheter (e.g., central venous catheters ("CVCs"), peripherally inserted central catheters ("PICCs"), peripheral intravenous catheters ("PIVs"), sheaths, etc.). Some vascular access catheters come mounted on a needle ("over the needle" or "OTN" catheters). Some OTN catheters also include an integral guidewire. The needle safety assembly 102 as described herein can secure the sharp tip of the needle and allow the guidewire to remain in the patient and extend outside the medical device. Ultrasound is commonly used during the insertion of vascular access catheters. The ultrasound can help with advancing the needle, the guidewire, and finally the catheter itself. Many OTN catheter insertion techniques require the use of two hands to insert the guidewire and/or catheter into the vasculature of a patient. In particular, catheters longer than about 1.5 inches typically require some type of two-handed insertion. One drawback of the two-handed techniques is that the ultrasound probe must be put down at some point during the insertion, and the loss of ultrasound visualization can lead to failure to successfully advance the guidewire and/or catheter. Also, two-handed techniques are technically more difficult, and require more skilled medical professionals to perform the insertion, while not securing the needle-sharp tip passively and may require additional manipulation by the medical professional.

The needle safety assembly 102 can be used as part of a catheter inserter. The catheter inserter operates to insert a catheter into the body of a patient, e.g., a human or animal. The needle safety assembly 102 can be sized to fit within catheter hubs. Thus, embodiments of the present needle safety assembly 102 can be used with catheter hubs and leave the guide wire or other medical device extending past the catheter hub toward the patient.

The needle safety clip, in some embodiments, is formed from a unitary body that has a resiliency to be deformed elastically when a needle extends past the clip. The clip thus stores energy. When the needle-sharp end is retracted into the clip, the energy, e.g., the energy in the flexed part of the clip 107, is released and the clip's distal end moves to a safety position covering the sharp end of the needle. The clip in its safety position returns to its original size and shape. The clip now resists deformation while allowing a medical device that is smaller than the needle, e.g., a guidewire, to extend through the clip.

Needle safety devices are used to cover the needle tip after use, and can be passive or active. Active devices need to be activated by the user (e.g. by folding a plastic sheath over the needle), whereas passive devices do not require user activation (i.e. the needle safety device is automatically deployed without user intervention). In passive needle safety clips, the needle tip is withdrawn from the catheter hub; the safety clip is deployed to cover the tip of the needle. Examples described herein allow the clip to deploy correctly if a device (e.g., a guidewire) is present and extends past the end of the needle tip. The presently described clip has a unitary body as opposed to a more complicated multiple body needle safety system. Multi-body safety systems are more complicated safety mechanisms that can also interfere with normal use of the medical device (e.g., they may generate excessive friction during catheter advancement over the needle, or require excessive force when removing the needle safety mechanism from the catheter hub). Thus, there is a need for a one-piece, passive needle safety device that functions when a medical device (e.g., a guidewire) is present and extending past the needle tip, and does not interfere with normal device function when compared to a similar device without needle safety.

Figure 19:
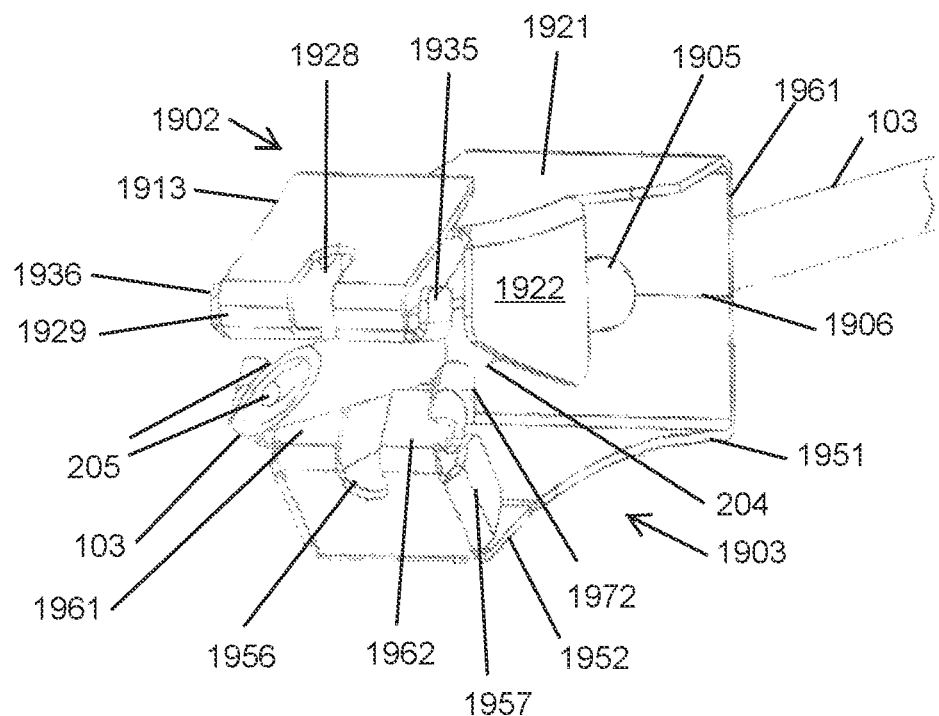
FIG. 19 shows a perspective view of a needle safety clip in a use position according to an embodiment.

FIG. 19 shows a needle safety clip 1900 in a use position with a needle 103 extending through the needle safety clip. A proximal wall 1901 joins a first, upper arm 1902 and a second, lower arm 1803, which are forced apart by the needle 103 extending between the arms 1902, 1803. The proximal wall 1901 includes an aperture 1905 through which the needle 103 extends. The needle 103 can freely travel distally through the aperture 1905 even with the ends of the clip arms 1902, 1903 pressing against the needle 103. In operation, the needle 103 can extend distally from the clip 1900, and out of a medical device, e.g., a catheter or other insertion device, to engage a patient's body, e.g., insertion into a patient's vasculature. The needle safety clip 1900 further includes a through aperture even with the needle's sharp tip covered by the needle safety clip.

The proximal wall 1901 is generally planar and has a thin wall, e.g., a width of less than about 0.0035 inch, +/−0.0005 inch. The proximal wall 1901 can be formed from a single body, e.g., a metal, steel, stainless steel, or a rigid polymer. The aperture 1905 to receive the needle is centrally positioned in the proximal wall 1901. The proximal wall 1901 can also define a center plane of the needle safety clip 1900. The center plane can extend essentially normal to the body of the proximal wall and contain the center line that is intermediate the upper edge and the lower edge. The center plane can bisect the aperture 1905. The center plane can include the center line 1906.

The upper arm 1902 extends distally from the top edge of the proximal wall 1901. The upper arm is cantilevered from the proximal wall 1901. The upper arm 1902 can be formed from a same blank (of metal or polymer) as the proximal wall 1901. The upper arm 1902 has a thin wall, e.g., a width of less than 0.01 inch. The upper arm wall 1902 can be formed from a single body, e.g., a metal, steel, stainless steel, or a rigid polymer. The upper arm 1902 can be shaped to allow the upper arm 1902 to bend upwardly (relative to FIGS. 19-25). This allows the upper arm 1902 to spread away from the lower arm 1903 to allow the needle to pass thereby when in a use position. However, the resting state of the upper arm 1902 in a closed, safety position (FIGS. 23-27). When the needle 103 is removed from contacting the end of the upper arm 1902 or the upper arm is not forced open, the upper arm 1902 will move toward the bottom of the clip, e.g., the lower arm 1903 or the bottom of the clip.

At least part of a free end of the upper arm moves past the center plane of the safety clip 1900. The upper arm 1902 includes an opening, e.g., a slot 1928, that is smaller in a lateral dimension than the needle 103. Thus, the needle 103 is not received in the slot 1928 with the needle in the use position. The slot 1928 aligns, at least partly, with the aperture 1905 when the upper arm is in the safety position (FIGS. 23-27).

The upper arm 1902 includes a first part 1911 joined to the proximal wall 1901. The first part 1911 has essentially planar outer and inner surfaces. The first part 1911 has a lateral first dimension that is essentially the same as the width of the proximal wall 1901. The first part 1911 narrows in width as it transitions to an upper arm, second part 1912. The second part 1912 has essentially planar outer and inner surfaces. The second part 1912 has a lateral second dimension that is narrower than the first dimension. The second part 1912 can also be longer than the first part 1911. The second part 1912 includes straight sides, and in an embodiment, the straight sides can be parallel to each other. A transition from the second part 1912 to an upper arm, third part 1913 can change in lateral dimension as it transitions to the third part 1913. The third part 1913 includes a plurality of essentially planar outer and inner surfaces. The third part 1913 can have a third dimension that is wider than the lateral dimension of the second part 1912 and the same or smaller than the first dimension of the first part 1911. The third part can be about as long as the second part 1912 and longer than the first part 1911.

The second part 1912 of the upper arm 1902 includes a sidewall 1922, 1923 on each side of the body of the second part. The side walls 1922, 1923 extend downwardly from the second part 1912 toward the lower arm 1903 from opposite sides of the second part 1912. The sidewalls 1922, 1923 can be mirror images of each other. The sidewalls 1922, 1923 can extend over half the length of the second part 1912, e.g., substantially the entire length of the second part 1912. The sidewalls 1922, 1923 have a height that allows the ends of the upper arm and the lower arm to move to the closed position before contacting the lower arm 1903. The free edge of the sidewalls 1922, 1923 can be non-parallel to the second part 1912 such that the free edge follows closely the lower arm in the closed, safety position of the needle safety clip 1900.

The third part 1913 of the upper arm 1902 includes a plurality of bends to create needle engaging surfaces in both the use position and the safety position. The first bend at the joint 1925 between the second part 1912 and the third part 1913 extends the third part upwardly from the second part 1912 (see, e.g., FIGS. 19-20, 22, 24, 25 and 32). A flat wall 1926 extends upwardly from the joint 1925. A further bend is formed at the distal edge of the flat wall 1926, which bends downwardly into a main body 1927 of the upper arm, distal third part 1913. The main body 1927 has a planar surface extending distally in which is formed the upper arm slot 1928. The main body 1927 continues with a finger 1929 in each side of the slot 1928. A knuckle 1931 is formed at the distal edge of the main body 1927, which curves downwardly about ninety degrees, to form a first finger section 1932. This curves the finger section 1932 downwardly and distally. A second finger section 1934 follows a knuckle 1933 at the distal edge of the first finger section 1932. The second knuckle 1933 further bends the finger distally to such that the second finger section 1934 is essentially flat against the needle 103 when the safety clip 1900 is in the use position. A further bend extends along the outer side of the second finger section 1934 to form upstanding sidewalls 1935, 1936. The sidewalls 1935, 1936 extend upwardly toward the main body 1927. A needle securing pocket, e.g., interstice, is formed between the main body 1927, the finger section 1932, the finger section 1934 and the side walls 1935, 1936.

The lower arm 1903 extends distally from the bottom edge of the proximal wall 1901. The lower arm 1903 is cantilevered from the proximal wall 1901. The lower arm 1903 can be formed from a same blank as the proximal wall 1901 and the upper arm 1902. The lower arm 1903 includes a proximal first part 1951 connected to the proximal wall 1901. The first part 1951 has a lateral first dimension that is essentially the same as the width of the proximal wall 1901. The first part 1951 narrows in width as it transitions toward a lower arm, second part 1952. The first part 1951 can have a lateral second dimension that is smaller than its first dimension. The first part 1951 extends most of the length of the lower arm 1903. The second dimension of the first part 1951 is of a width greater than the dimension of the vertically aligned part of the upper arm 1902. The side walls 1922, 1923 may contact the lower arm first part 1951 if the arms close together far enough. The second part 1952 has essentially planar outer and inner surfaces. The second part 1952 has a lateral third dimension that is narrower than the first dimension at the first part 1951. The second part 1952 can also be shorter, in the longitudinal direction than the first part 1951. The second part 1952 includes straight sides that angle inwardly in the distal direction. A transition from the second part 1952 to a lower arm, third part 1953 can be the same lateral dimension as it transitions from the end of the second part 1952 to the third part 1953. The third part 1953 includes a plurality of essentially planar outer and inner surfaces. The third part 1953 can have a fourth dimension that is less than the lateral dimension of the first part 1951. The third part 1953 is shorter than the first part 1951.

The third part 1953 includes the opening that forms the lower arm slot 1956. The slot 1956 is formed by fingers 1961, 1962 that extend alongside the slot. The third part 1953 at the fingers 1961, 1962 bends back distally to form a surface at which the needle 103 can be supported.

Outwardly from the slot 1956 and the outer edges of the fingers 1961, 1962, latches 1971, 1972 are formed. The latches 1971, 1972 extend upwardly and outwardly from the fingers 1961, 1962, respectively. The latches 1971, 1972 cantilever from the edge of the fingers. The latches 1971, 1972 include a curved top surface and remain outwardly of the needle in the use position. The latches 1971, 1972 are moved inwardly to engage the upper arm third part 1913 when in the safety position (See, e.g., FIGS. 23-26).

Figure 20:
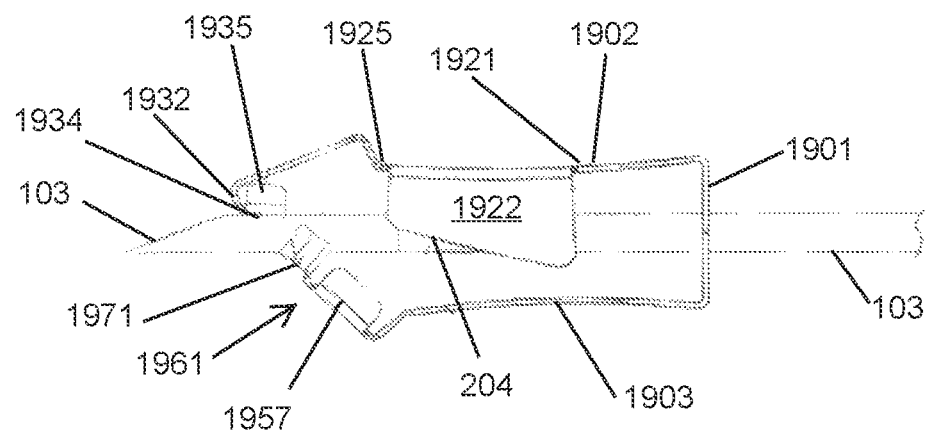
FIG. 20 shows a side view of a needle safety clip in a use position according to an embodiment.

FIG. 20 shows an elevational side view of the needle safety clip 1900 in the use position with the needle-sharp end extending distally (leftward in FIG. 20) of the distal end of the clip 1900. The upper arm 1902 rides on a needle surface at the downward surface of the section 1932 of the third part 1913. The lower arm 1903 rides on the needle surface at the upward surfaces of the fingers 1961, 1962. The needle 103 is rigid enough to hold its shape against the inwardly urging spring forces of the upper arm 1902 and the lower arm 1903. The needle 103 can be moved proximally, limited by the needle stop 2004 and the proximal wall aperture 1905, and distally against the spring force impinged thereon by the arms 1902, 1903. The needle 103 is intermediate the upper arm sidewalls 1922, 1923. The needle 103 extending through the clip 1900 bends the upper arm 1902 upwardly and the lower arm 1903 downwardly against the resting position of the arms 1902, 1903. Thus, when the needle 103 is withdrawing from the free ends of the arms 1902, 1903, the arms 1902, 1903 return to the rest position and secure the needle-sharp end within the clip 1900.

Figure 21:
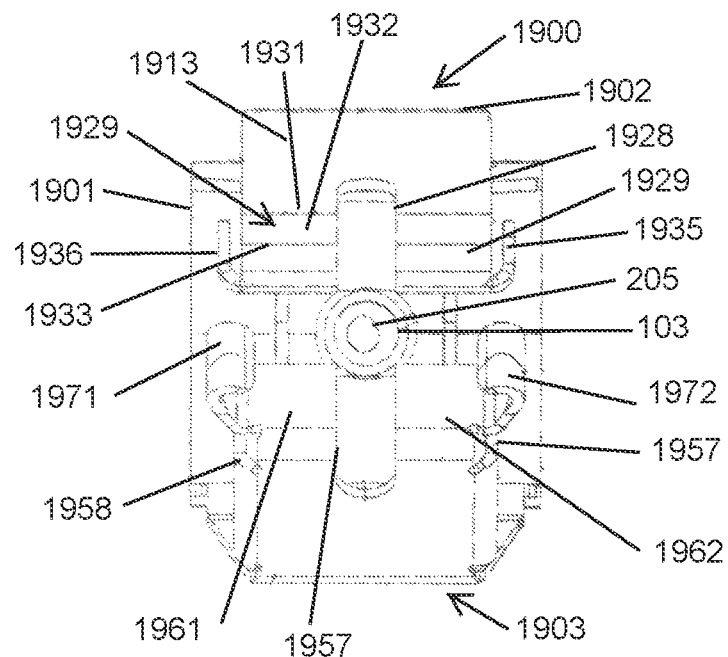
FIG. 21 shows a distal end view of a needle safety clip in a use position according to an embodiment.

FIG. 21 shows a distal end view of the clip 1900 with the needle extending past the arms 1902, 1903. As can be seen in FIG. 3, the needle 103 has a diameter that is larger than the recesses 1928, 1956. Thus, the needle 103 rests on the surfaces of the upper arm third part 1913 and the lower arm third part 1955. The medical component, e.g., a guidewire 205, is sized such that its diameter or other dimension is less than the lateral width of both slots 1928, 1956. In an example, both slots 1928, 1956 have the same width. The slots 1928, 1956 can have different lengths. The arms 1902, 1903 may close to secure the needle 103 but the guidewire may extend out of the distal end through the slots 1928 and 1956.

Figure 22:
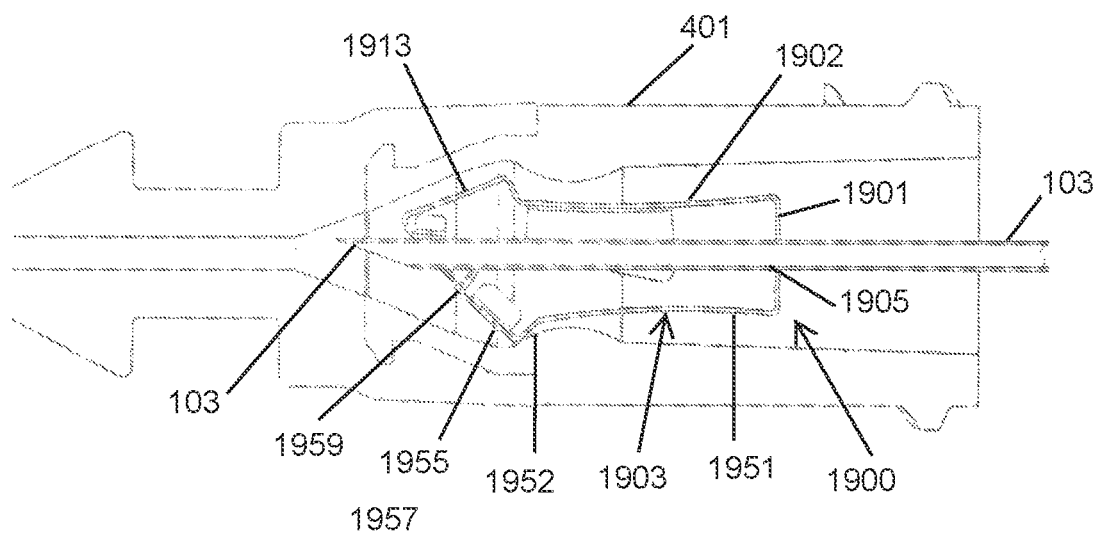
FIG. 22 shows cross sectional view of a needle safety clip in a catheter hub at the use position according to an embodiment.

FIG. 22 shows cross sectional view of the needle safety clip 1900 mounted with a needle 103 in the use position. The needle clip 1900 is positioned in a catheter hub 401. The catheter hub 401 may be positionable in a catheter insertion device. The needle clip 1900 holds the needle 103 aligned with a port in the catheter hub 401 such that the needle can move distally out of the hub to engage a patient's body.

Figure 23:
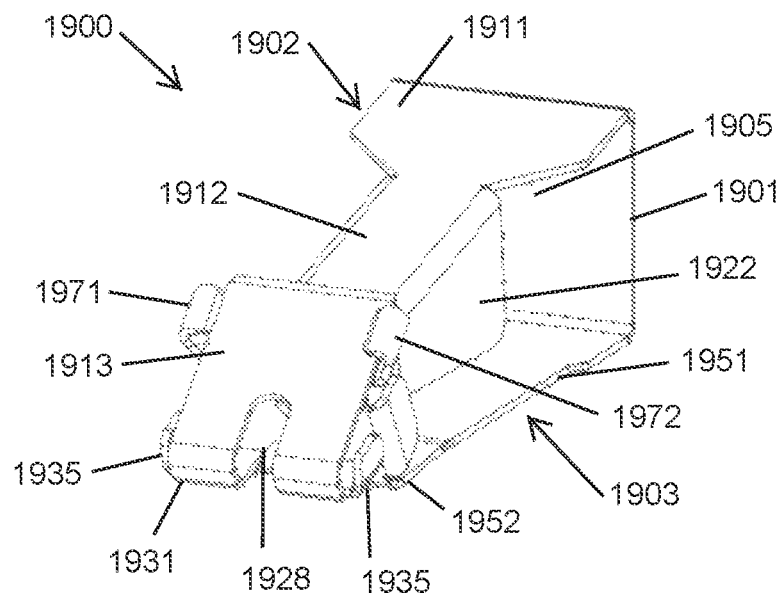
FIG. 23 shows a perspective view of a needle safety clip in a safety position according to an embodiment.

FIG. 23 shows a front perspective view of the needle safety clip 1900 on the safety position. A needle is not shown in FIGS. 23-27 for clarity. The distal end of the upper arm 1902 has moved downwardly toward the lower arm 1903. The distal end of the lower arm has moved upwardly toward the upper arm 1902. The side walls 1922, 1923 are closely adjacent the lower arm 1903. The distal ends of the upper arm 1902 and the lower arm 1903 overlap such that at least part of the slots 1928, 1956 align with the proximal wall aperture 1905. See, e.g., FIG. 27. In some embodiments, one of the arms 1902, 1903 moves toward the center a greater extent than the other. In an example, the lower arm 1903 is essentially stationary and the upper arm 1902 moves toward the lower arm. The latches 1971, 1972 extend upwardly from the lower arm 1903 and around the outer sides of the upper arm 1902, respectively, to engage the upper arm 1902. The latches 1971, 1972 will stop the upper arm 1902 from moving away from the lower arm 1903. This will help prevent access to the needle-sharp end after the clip 1900 enters its safety position.

Figure 24:
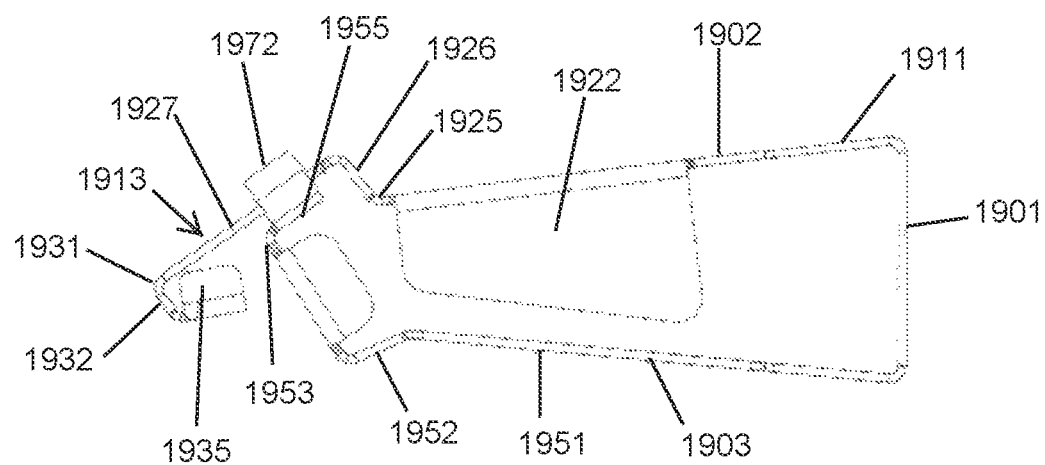
FIG. 24 shows a side view of a needle safety clip in a safety position according to an embodiment.

FIG. 24 shows a side elevational view of the safety clip 1900 in the safety position. The distal end of the top arm 1902 at the third part 1913 extends past the third part 1955 of the lower arm 1903. The latch 1972 extends up and over the upper arm third part 1913. The bottom edge of the side wall 1922 is generally parallel to first part 1951 of lower wall 1903. The distal end of the top arm 1902 distal to the latch 1972 extends forwardly and then turns back toward the third part 1955 of the lower arm 1902.

Figure 25:
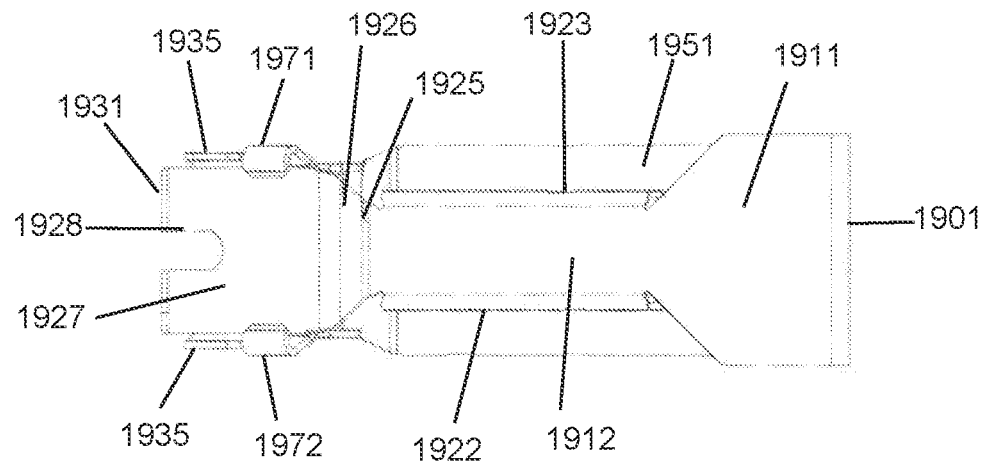
FIG. 25 shows a plan view of a needle safety clip in the safety position according to an embodiment.

FIG. 25 shows a top, plan view of the clip 1900 in the safety position. The sidewalls 1922, 1923 extend downwardly toward the first part 1951 of the lower arm 1902. The recess 1928 begins distally of the third part 1913 of the lower arm 1902. Both the latches 1971, 1972 extend above the main body 1927 of the upper arm third part 1913 and engage the main body 1927 to hold the upper arm 1902 in the safety position relative to the lower arm 1903.

Figure 26:
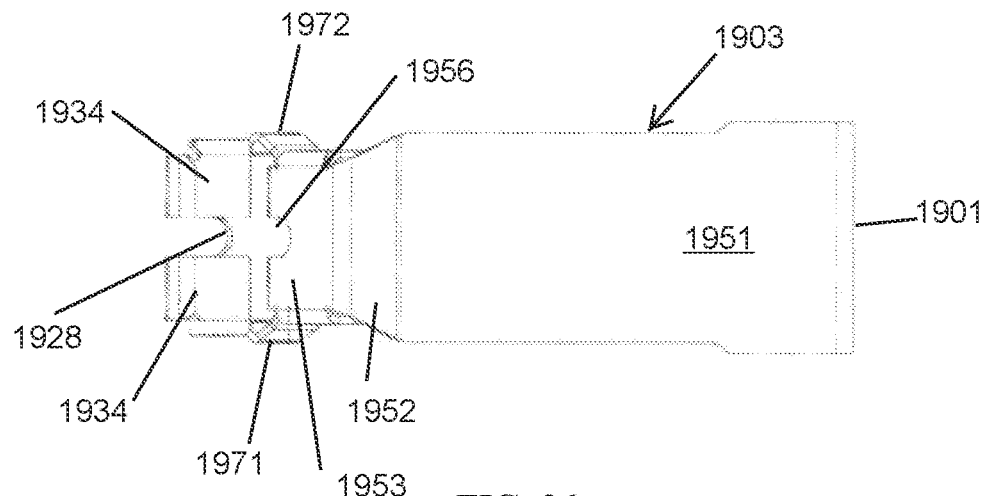
FIG. 26 shows a bottom view of a needle safety clip in the safety position according to an embodiment.

FIG. 26 shows a bottom view of the clip 1900 in the safety position. The bottom arm 1903 is wider than the top arm so the top arm is only visible where the top arm 1902 extends distally past the lower arm 1903 or is wider at the distal end. The slots 1928, 1956 are aligned to allow the guidewire, or medical device to extend past through the slots.

Figure 27:
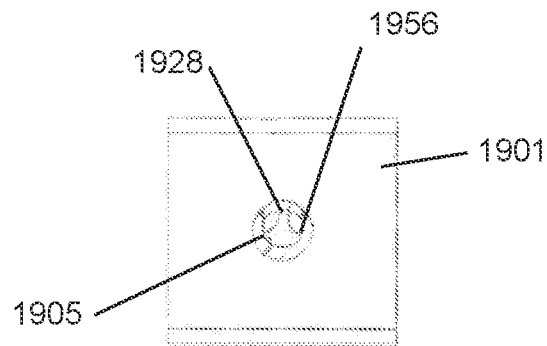
FIG. 27 shows a proximal end view of a needle safety clip in a safety position according to an embodiment.

FIG. 27 shows the proximal end view of the safety clip 1900 at the proximal wall 1901. This is in the closed position. The aperture 1905 aligns with the slot 1928 and the slot 1956. Thus, a guidewire or other medical device can extend through the needle and through the safety clip 1901, e.g., through the proximal wall aperture 1905 and both slots 1928, 1956 in the arms 1901, 1902.

Figure 28A:
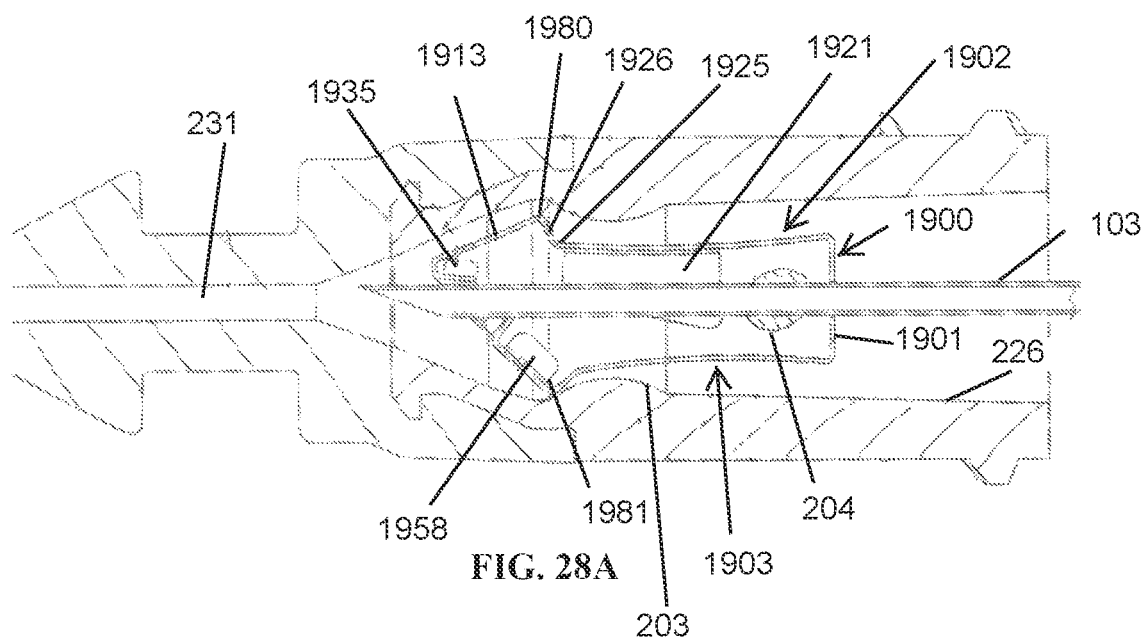
FIG. 28A shows a cross section view of a needle safety clip in a catheter hub, in the use position, according to an embodiment.

FIG. 28A shows a view of a needle safety clip 1900 in a medical device, which can be part of a catheter inserter or a catheter hub 225. The catheter hub 225 includes a cavity 226 that defines an open interior of the hub 225. The clip 1900 can be loaded with a needle 103 and then inserted into the cavity 226 past the guide 230. The guide 230 can include at least two protrusions into the cavity 226 near the distal (leftward) end of the cavity 226. The protrusion 230 can be annular around the interior wall of the cavity 226. The clip 1900 holds the needle 103 aligned with the central longitudinal through-hole 231 at the distal end. The needle stop 204 prevents the needle 103 from moving distally out of the clip 1900 past the proximal wall 1901.

Figure 28B:
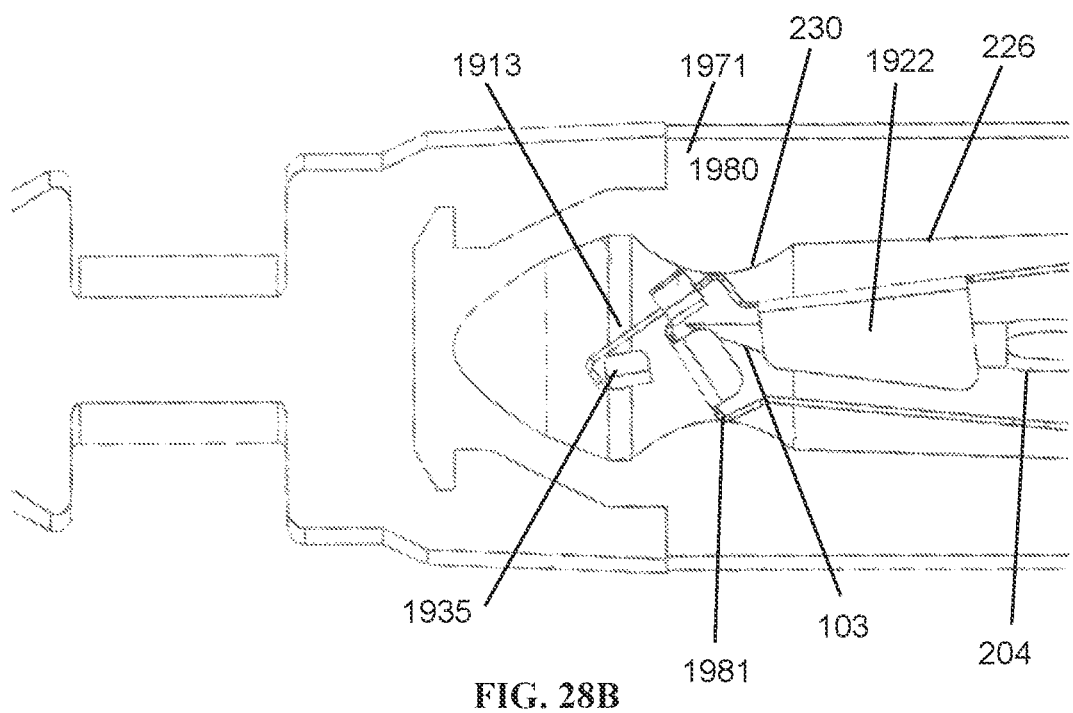
FIG. 28B shows a cross section view of a needle safety clip in a catheter hub, in the safety position, according to an embodiment.

FIG. 28B shows a view similar to FIG. 28A but with the needle safety clip 1900 transitioned to the safety position and being retracted out of the distal end of the catheter hub 225. The upper arm 1902 is in contact with the protrusion 230 at the top of the cavity 226, e.g., at the point 1980 at the bend between the part 1926 and part 1913. The lower arm 1903 is in contact with the protrusion 230 at the bend 1981 between the part 1952 and part 1953. The latches 1971, 1972 both extend from the lowest point of the lower arm 1903 farther than the open distance between in the protrusions 230 in the cavity 226. The latches 1971, 1972 are deflected when the clip 1900 moves past the protrusions 230 such that the latches are bent over the top of the upper arm 1902, e.g., over the main body 1927 of the distal, third part 1913 of the upper arm 1902. In an example, the latches 1971, 1972 engage the top wall of the cavity at a protrusion 230 at the same time the bottom part of the lower arm 1903 engages the bottom wall of the cavity, e.g., at a protrusion 230. The vertical distance between the top end of the latches 1971, 1972 and the bottom of the lower arm 1902 is greater than the vertical distance in the cavity 226. When the latches 1971, 1972 are bent over the upper arm 1902, the upper arm becomes latched to the lower arm 1903. This may reduce the likelihood that a needle can be worked free from the clip 1900.

Figure 29:
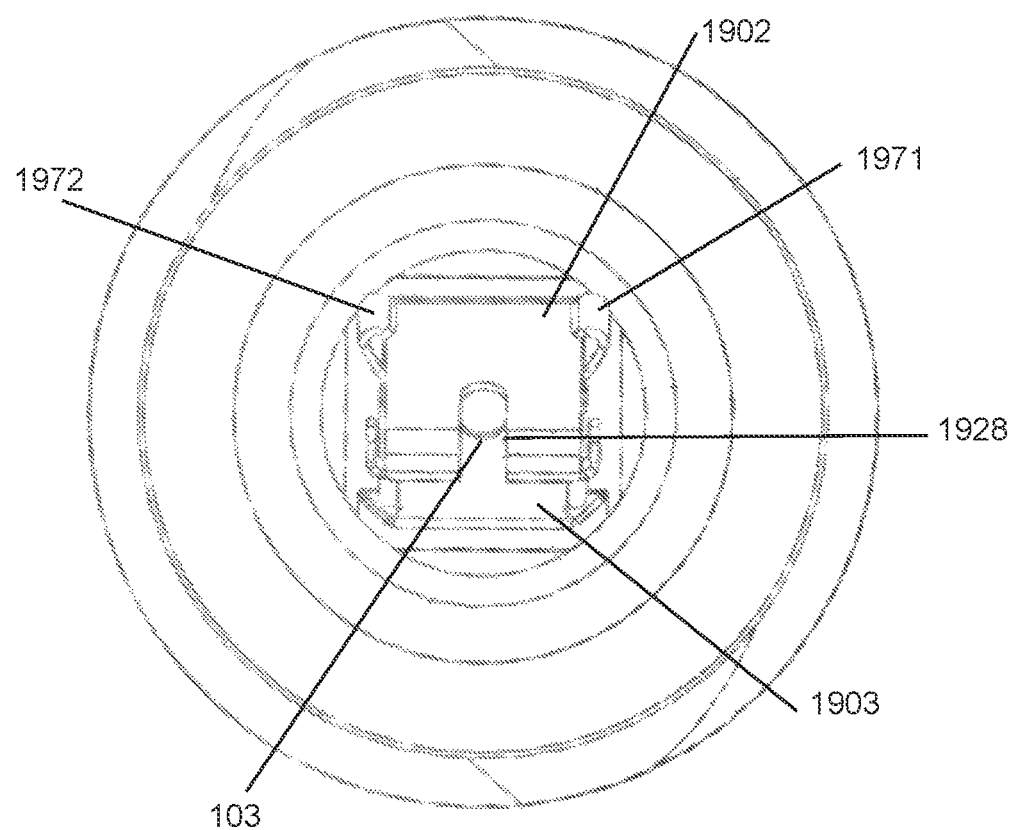
FIG. 29 shows a distal end view of a needle safety clip in a catheter hub, in the safety position, according to an embodiment.

FIG. 29 shows a distal end view of the catheter hub 225 with the needle safety clip 1900 therein in the safety position. The latches 1971, 1972 are over the top arm 1902. The distal end of the upper arm 1902 is partially over the distal end of the lower arm 1903. The slots 1928, 1956 are aligned with the needle 103 being trapped between the distal end of the lower arm 1903 and the proximal wall 1901. The lower arm's slot 1956 is narrower than the diameter of the needle 103. The proximal wall aperture 1905 (not shown in FIG. 29) is smaller than the needle block 204.

As can be seen in the figures, the needle safety clip 1900 includes a second, bottom arm with includes a main body 1951 that is wider than a main body 1912 of the first, upper arm 1902.

The needle safety clip 1900 includes the first, upper arm main body 1902 that is cantilevered from the proximal wall 1901. The first, upper arm main body 1902 includes two side walls 1922 extending toward the second arm main body 1951.

The two side walls 1922 of the first arm main body 1951 are essentially planar and extend between the distal end of the first, upper arm 1902 and the proximal end of the first, upper arm 1902.

The needle safety clip 1900 can include fingers to form the slots 1928, 1956. The upper, first arm 1902 includes a first finger 1929 (left in FIG. 23) and a second finger 1929 (right in FIG. 23) that form the slot 1928 therebetween, wherein both the first finger and the second finger include a sidewall 1938 between which the needle 103 extends, e.g., in both the use position and the safety position.

Unlike some clips on the market today, the first arm main body 1911, 1912 and the second arm main body 1951 do not intersect in an example embodiment. The first arm main body 1911, 1912 can be elongate and include flat sections joined by bends in the body of the material. The second arm main body 1951 can be elongate and include flat sections joined by bends in the body of the material.

In an example, the proximal wall 1901 of the needle safety clip 1900 is planar and the proximal wall aperture 1905 has a dimension greater than a main needle part, e.g., the needle block 204. The dimension of the main needle part is smaller than a profile change in the needle to prevent the needle from exiting proximally past the proximal wall 1901 through the aperture 1905.

The first, upper arm 1902 includes a first dimension, e.g., a width at a first location, adjacent the proximal wall 1901 and a second dimension, e.g., a width at a second location, smaller than the first dimension distally from the first dimension. A third dimension of the first, upper arm 1902 is greater than the second dimension distally from the second dimension. The second, lower arm 1903 includes a fourth dimension adjacent the proximal wall 1901 and a fifth dimension smaller than the fourth dimension distally from the fourth dimension and the proximal wall.

Figure 30:
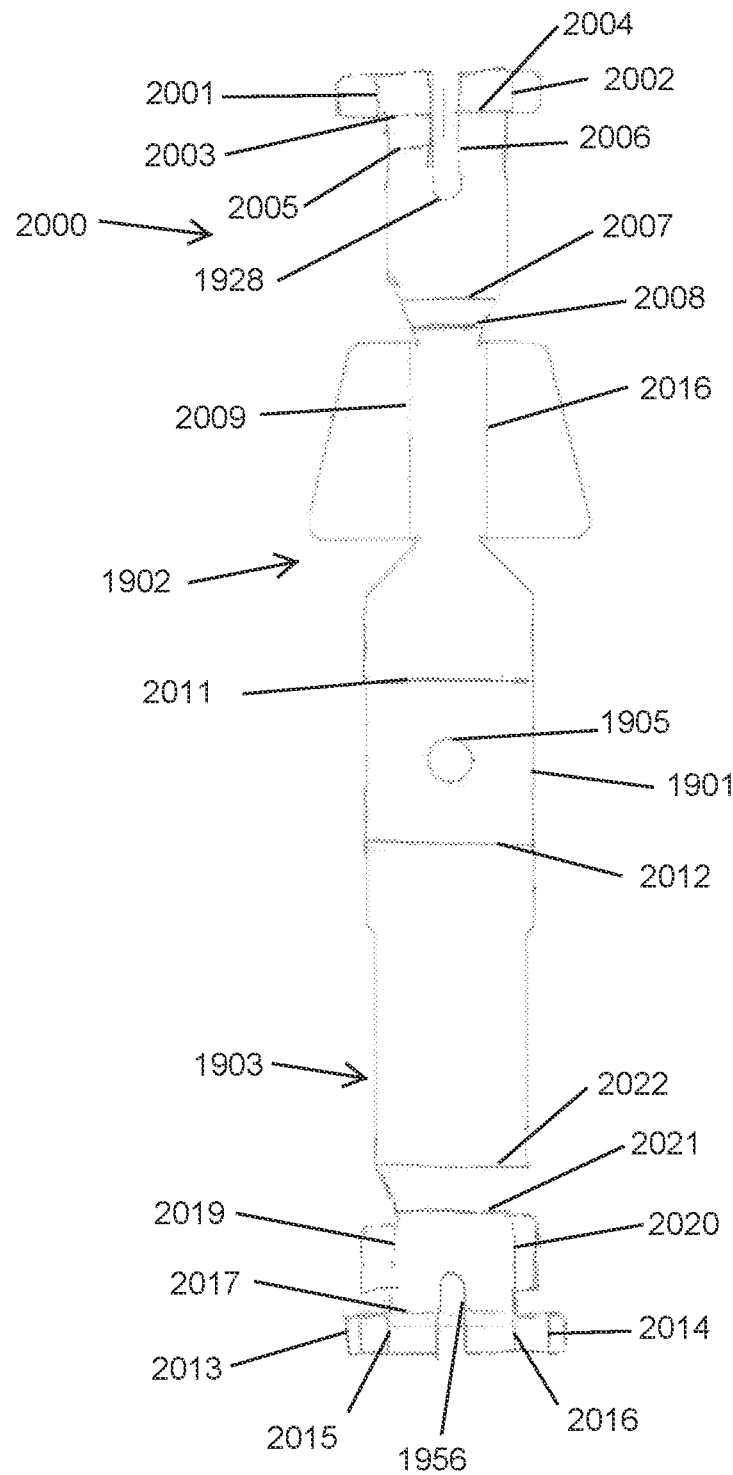
FIG. 30 shows a blank to be formed into a needle safety clip according to an embodiment.

FIG. 30 shows a blank 2000 that can be formed into the needle safety clip 1900 as shows in FIGS. 19-29. The blank 2000 can be a unitary piece of sheet metal that can be formed into the clip 1900. The blank 2000 can be stamped out of stainless steel, e.g., a thickness of about 0.0030 inch, +/−0.0005 inch to about 0.0040 inch, +/−0.0005 inch, or about 0.0035 inch, +/−0.0005 inch. Other medical grade metals can be used to form the blank. The blank 2000 has a resiliency to allow for bending of the body thereof and can retain its shape and be deflected from its rest state and the material thereof will urge the body to its rest state. The rest state will be the safety position with the needle-sharp end covered by the formed clip 1900.

Starting at the top end, the blank 2000 is bent at lines 2001, 2002 to form the side walls on the top arm fingers. In an example, the bend is ninety degrees. The blank 2000 is bent at 2003, 2004 to begin to form the knuckle 1933 in the fingers 1929 on the top arm distal part 1913. In an example, this bend is about sixty-five degrees. The blank 2000 is bent at 2005, 2006 to form the knuckle 1931 in the fingers 1929 on the top arm distal part 1913. All of these bends occur before the closed end of the slot 1928. The transition from the top arm distal part to the top arm intermediate part is made at bends 2007, 2008. Bend 2007 can be in a different direction than the bend 2008. Bend 2007 can be about eighty-eight degrees in a first direction, e.g., in the same direction as bends 2001-2005, which can be upward as shown in FIG. 30. Bend 2008 can be about sixty degrees in the other direction, e.g., downward into the paper as shown in FIG. 30. The sidewalls 1922, 1923 can be formed at bends 2009, 2010, which direct the sidewalls 1922, 1923 to be bent at about ninety degrees upwardly. At bend 2011, the top arm 1902 is defined relative to the proximal wall 1901. The bend 2011 may be about ninety-six degrees.

Referring now to the bottom end of the blank 2000 as shown in FIG. 30, the bottom arm 1903 is formed. At bends 2013, 2014, the catch ends of the latches 1971, 1972 are formed. The bends 2013, 2014 can be about fifteen degrees, downwardly. The free, catch ends from the bends 2013, 2014 can extend over the top arm in the safety position in an example embodiment. Further latch bends 2015, 2016 are made, downwardly about sixty-five degrees. At bends 2017, 2018, the knuckle, in the fingers of the bottom arm, is made. The bends 2017, 2018 can be about 86 degrees, upwardly. The bends 2017, 2018 are made intermediate the ends of the slot 1956, generally at a median of the slot length and can form the end wall 1959. At bends 2019, 2020, the sidewalls 1957, 1958 are formed. The bends 2019, 2020 can be upward at about ninety degrees. At bend 2021, the third part 1955 of the bottom arm 1903 is formed. Bend 2021 can be about eighty-three degrees upward. At bend 2022, the joint 1953 is formed between the first part 1951 of the lower arm 1903 and the second part 1952 of the lower arm. The bend 2022 can be about thirty degrees downwardly. At bend 2012, the lower arm 1903 is defined relative to the proximal wall 1901. The bend 2012 can be about ninety-five degrees.

While the present description describes the bends 2001-2022 in a specific order, the present disclosure is not so limited. The order of the bends 2001-2022 was described as a convenience of description starting at one end of the blank to the other end of the blank. The bends may be performed in a different order.

The surfaces of needle safety clip 1900 can be planar at its different parts intermediate the bends 2001-2022 as described herein.

Various embodiments of the present disclosure include a needle safety clip 1900 without the latches 1971, 1972. The needle safety clip 1900 is in the safety position and secures a needle. The needle-sharp end is held proximally the free end part 1913 of the top arm 1902 and the free end part 1955 of the lower arm 1903. The slots 1928 and 1956, as well as the aperture 1905 in the proximal wall 1901 are aligned. in an example, the center of the aperture 1905 is aligned with the center line of the slots 1928, 1956 such that a medical device that is smaller than the needle and slots 1928, 1956 can extend through the needle and the safety clip 1900 in its safety, e.g., closed, position. In the safety position, the free end parts, 1913, 1955 overlap, here shown with the top free end part 1913 extending beyond the bottom free end 1956. The bottom free end 1956 provides a blocking wall to keep the needle-sharp end from moving distally once the needle is retracted back into the safety clip past the bottom free end. When the needle-sharp end passes the bottom free end 1956, the bottom free end will move upwardly (as shown in the figures) to hold the needle in the safety clip 1900. Likewise, the top free end 1913 will move centrally when the needle-sharp end is retracted proximally there past.

The needle 103 can include the needle stop 2004. The needle stop 2004 can be a portion of the needle shaft that is enlarged, e.g., has at least a part thereof that has a larger outer diameter. The larger outer diameter can be an integral part of the part of the needle shaft, e.g., a thicker wall, or can be a protrusion that extends outwardly from the needle shaft. The needle stop has a dimension that is greater than the dimension of the proximal wall aperture 1905. In an example, the diameter of the needle stop is greater than the diameter of the aperture 1905. Thus, the needle stop prevents the needle from exiting completely through the aperture 1905, which would expose the needle-sharp end.

Figure 31:
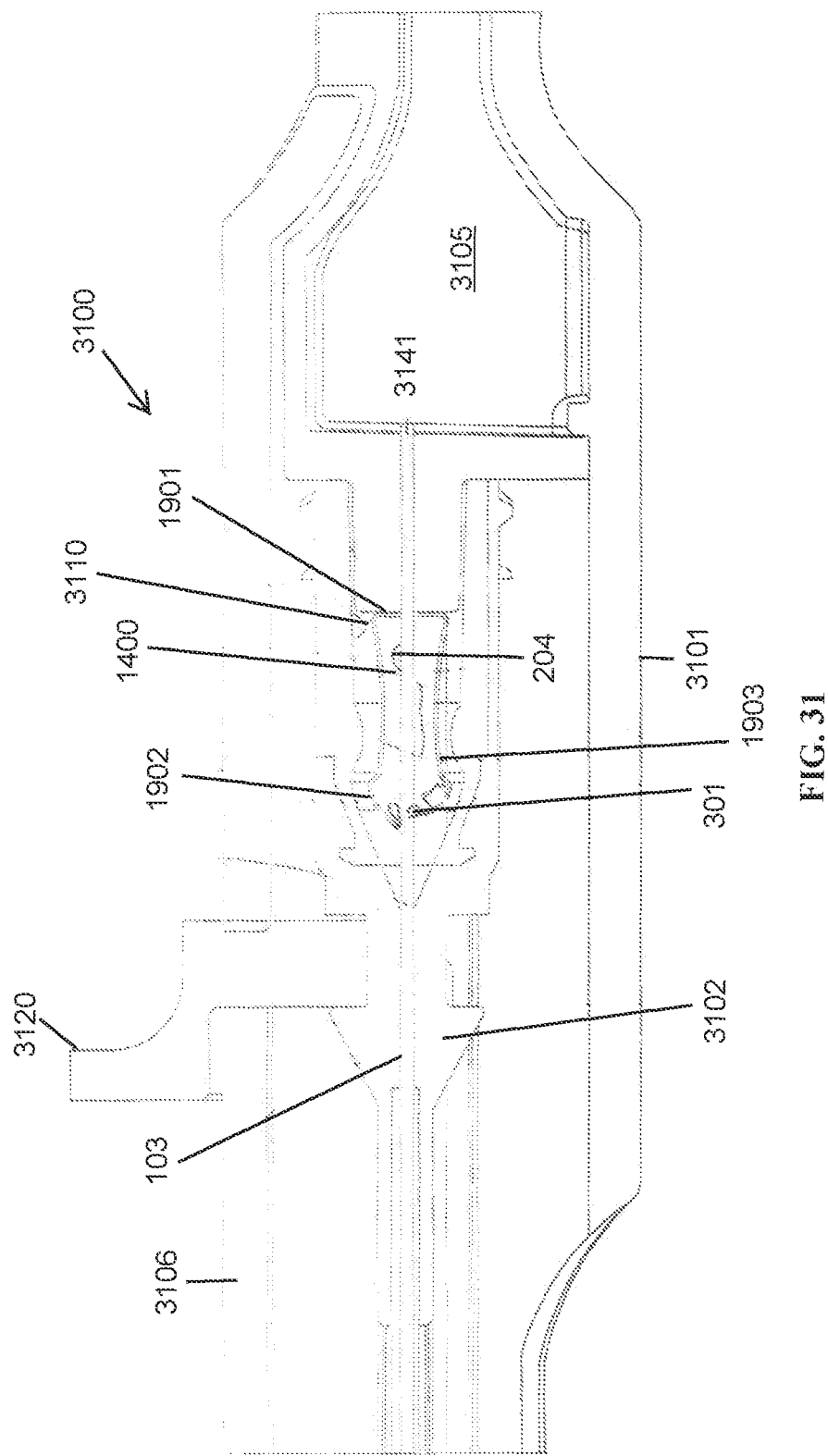
FIG. 31 shows a view of a medical device with a needle safety clip according to an embodiment.

FIG. 31 shows a catheter insertion device 3100, which includes a housing 3101 with an actuator slot 3106 to slidably receive an actuator 3120. The actuator 3120 can engage various moveable parts of the device, e.g., a catheter hub 3102. A proximal end 3141 of the needle 103 may be in fluid communication with a reservoir 3105. The needle safety clip 1900 may be mounted to the proximal end of the catheter hub 3102. The safety clip 1900 is releasably mounted in the recess 3104 in the proximal end of the catheter hub 3102. The needle 3102 may have a structure, e.g., a protrusion or other raised surface 204, which travels within the catheter hub (or the clip 1900) and engages the proximal wall 1901 of the needle safety clip 1900. The needle safety clip 1900 includes a moveable end (e.g., the distal ends of the upper arm 1902 and lower arm 1903) that closes after the needle's sharp end is moved distally past the moveable end. The proximal wall 1901 does not allow the needle 103 to travel proximally there past. The engaging structure 204 will prevent the needle from passing all of the way proximally through the needle safety clip 1900. Thus, the clip is released from the recess 3104 and remains on the end of the needle 103. In an example, when the catheter hub 3102 travels toward the distal end (left in FIG. 33), and exits the housing, the needle safety clip 1900 travels therewith. The arms 1902, 1903 of the needle safety clip 1900 close after the sharp end of the needle moved there past.

Figure 32:
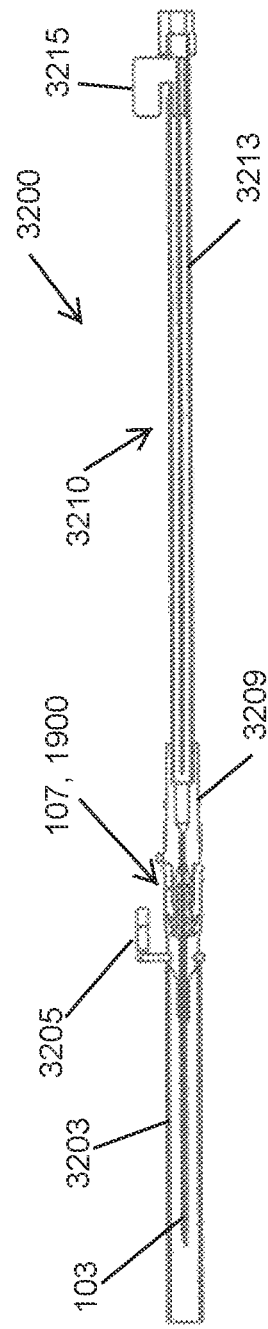
FIG. 32 shows a view of a medical device with a needle safety clip according to an embodiment.
Figure 33:
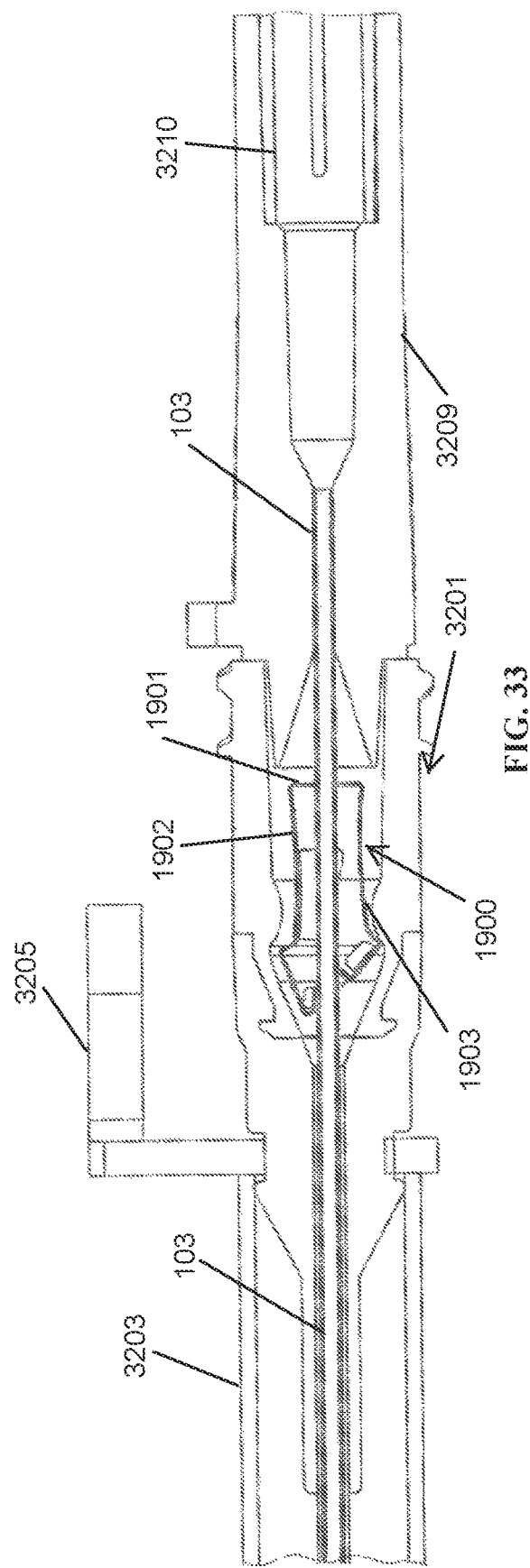
FIG. 33 shows an enlarged, partial view of the FIG. 32 medical device.

FIG. 32 shows a medical device 3200 with a needle safety clip 1900 according to an embodiment. FIG. 33 shows an enlarged, partial view of the medical device 3200. The needle safety clip 1900 may be mounted to a catheter hub 3201. The catheter hub 3201 may be similar to the catheter hubs described above (e.g., FIG. 22, 28A, 28B). A needle 103 may extend through the catheter hub 3201 such that it extends distally and proximally the hub 3201. A needle cap 3203 may extend distally from the hub before the medical device 3200 is used. The needle cap 3203 is removed prior to needle use. A distal handle 3205 is connected distally to the hub 3201. A user may engage the distal handle to control the device 3200 during insertion of the needle into a patient's body. With the needle 103 inserted into a patient's body, e.g., into the vasculature, the guidewire assembly 3210 is engaged to insert the guidewire 3211 through the catheter hub 3201, the needle safety clip 1900, and the needle 103 into the patient's body. The needle 103 provides an access path for the guidewire 3211. A guidewire housing 3213 extends proximally from the hub 3401 with a coupling 3209 therebetween. The coupling 3209 may be fixed to the proximal end of the needle 103. The guidewire 3211 is supported with the housing 3213. The user may engage a guidewire actuator 3215 to slide the guidewire 3211 distally from the user and through the needle 103. It is desired to leave the guidewire 3211 in the patient and remove the needle 103. In conventional devices, this exposes the needle-sharp end. The removal of the needle 103 in the device 3200, requires that the coupling 3209 be drawing proximally toward the user moving the needle 103 proximally relative to the hub 3201. When the needle's distal, sharp end passes the spring-loaded ends of the arms 1902, 1903 of the clip 1900, the arms close and cover the needle's sharp end. The guidewire 3211 extends through the clip 1900, e.g., though the aperture in the proximal wall 1901 and the slots both the arms 1902, 1903. The needle 103 can be completely retracted from the catheter hub 3201 and when it emerges from the hub, the needle's sharp end is covered by the safety clip 1900.

Figure 34:
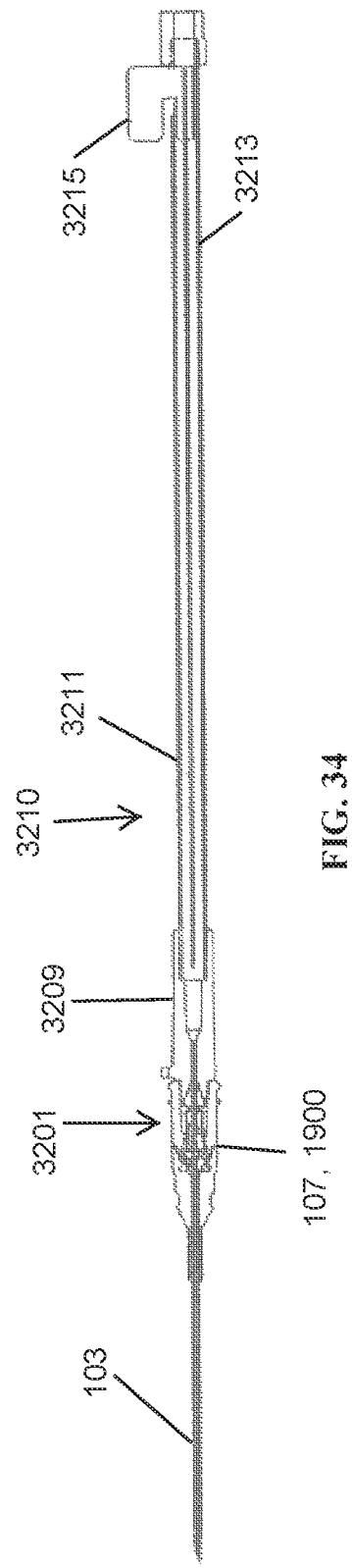
FIG. 34 shows a view of the FIG. 32 medical device at a different stage of use.

FIG. 34 shows the medical device 3200 at a different stage of use. The cap 3203 is removed from the distal end and the needle 103 is exposed. In this example, the handle 3205 was used to remove the needle cap 3203 and was released from the mating structure on the distal end of the catheter hub 3201.

Figure 35:
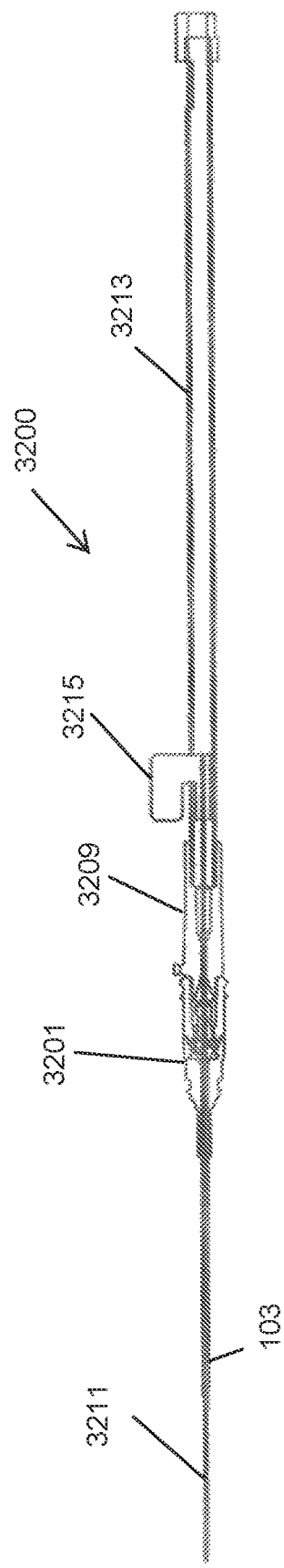
FIG. 35 shows a view of the FIG. 32 medical device at a different stage of use.
Figure 36:
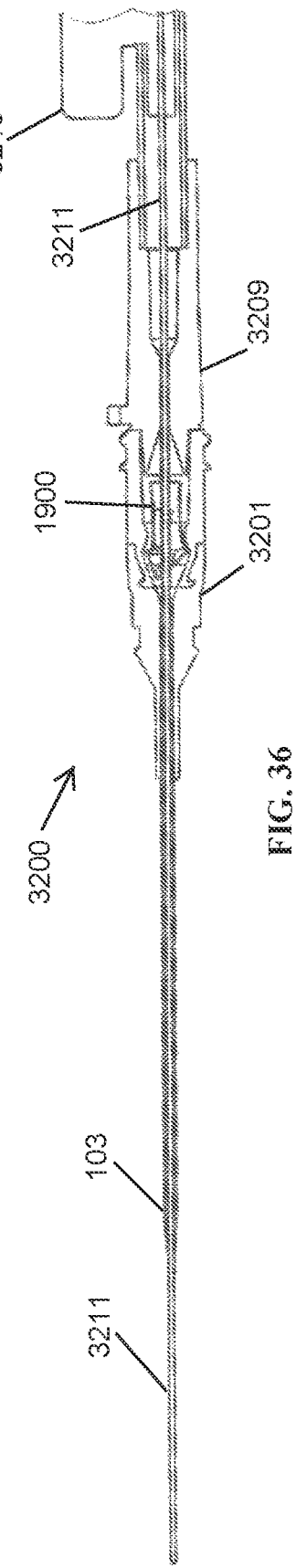
FIG. 36 shows an enlarged, partial view of the FIG. 35 medical device.

FIG. 35 shows the medical device 3200 in a different stage of use. FIG. 36 shows an enlarged, partial view of the medical device 3200 at the FIG. 35 different stage of use. The guidewire 3211 has been moved distally toward the patient through the coupling 3209, through the clip 1900, through the catheter hub 3201 and the needle 103. The distal end of the guidewire extends distally past the needle-sharp end. However, the guidewire 3211 also extends proximally past the needle safety clip 1900.

The medical device 3200 can be used as a vascular access catheter (e.g., central venous catheters ("CVCs"), peripherally inserted central catheters ("PICCs"), peripheral intravenous catheters ("PIVs"), sheaths, etc.). Some vascular access catheters come mounted on a needle ("over the needle" or "OTN" catheters). Some OTN catheters also include an integral guidewire. The needle safety clip 1900 as described herein can secure the sharp tip of the needle and allow the guidewire to remain in the patient and extend outside the medical device 3200. Ultrasound is commonly used during the insertion of vascular access catheters. The ultrasound can help with advancing the needle, the guidewire, and finally the catheter itself. Many OTN catheter insertion techniques require the use of two hands to insert the guidewire and/or catheter into the vasculature of a patient. In particular, catheters longer than about 1.5 inches typically require some type of two-handed insertion. One drawback of the two-handed techniques is that the ultrasound probe must be put down at some point during the insertion, and the loss of ultrasound visualization can lead to failure to successfully advance the guidewire and/or catheter. Also, two-handed techniques are technically more difficult, and require more skilled medical professionals to perform the insertion, while not securing the needle-sharp tip passively and may require additional manipulation by the medical professional.

FIG. 37 shows a perspective view of a catheter inserter 3700. FIG. 38 shows an inverted, cross-sectional view of the catheter inserter 3700. The catheter inserter 3700 operates to insert a catheter into the body of a patient, e.g., a human or animal. Catheter inserter 3700 includes a housing 3701 that is elongate and has a thin wall to define an open interior between a distal end 3702 and a proximal end 3703. The proximal end 3703 can be closed and integrally formed with the elongate, hollow body of the housing 3701. The distal end 3702 is open so that various components, e.g., the needle, a guidewire 3711, and/or catheter, can extend outside the housing. A seal 3705 may be positioned on the distal end 3702. The seal 3705 can be frangible, in an example, to allow components to be pressed therethrough. The seal 3705 may include a slit extending along a diameter that allows small components to extend therethrough but not allow larger objects therethrough. Such larger objects (e.g., the catheter hub) may force the seal 3705 off the distal end 3702. The housing 3701 can include a flat portion 3704 adjacent the distal end 3702 and on the opposite side of the housing from the actuator 3725. A frame 3709 is positioned on the housing 3701 and at least partially around the housing. The frame 3709 can encompass the flat portion 3904 and define a slide track for the actuator 3725. The frame 3709 can include ribs that extend longitudinally along the sides of the housing and lateral webs that extend around the housing. Additional webs can be provided on the flat portion 3704 to provide additional grips for the user's hand. The frame 3709 can be adhered to the housing or integrally formed with the body of the housing 3701. The housing 3701 may be other shapes that are elongate and have an open interior to receive other components. The housing 3701 can be formed of a rigid polymer and portions thereof may be transparent. With the housing 3701 being transparent, the internal components in the housing 3701 of the catheter inserter 3700 can be viewed while operating. The housing 3701 is adapted to support an actuator assembly 3725 that selectively engages a catheter assembly 3730 to move these assemblies relative to the housing. The housing 3701 further supports a needle 103 in a fixed position to insert into the patient's body and a retracted position after the guidewire 3711 is inserted into the patient's body. The housing 3701 includes a slot 3706 adjacent the distal end 3702 that aligns with the actuator assembly 3725 and allows the actuator assembly to be inside and outside the housing. A needle support 3708 is positioned at the distal end 3702. The support 3708 includes an aperture held by radial supports to support the needle 103 when the device is in use. As a result, the user need not use a second hand to support the needle 103, which tends to bend due to its length, narrow width and thin wall. In a use case, the catheter inserter 3700 can be used with one hand of the medical professional. The other hand of the medical professional can be free to engage the patient or perform other tasks, e.g. holding an ultrasound probe.

The actuator assembly 3725 includes an actuator that is adapted to slide on or in alignment within the frame 3709 on a top surface of the housing 3701. In an example, the actuator has a width that is essentially the same as or slightly less than a slide path of the frame 3709. Actuator can include at least one upraised ridge extending away from the housing 3701 and providing an engagement surface for a user's thumb or finger. The actuator further includes a recess (not shown) in the bottom thereof. Actuator assembly 3725 further includes a shuttle with an outer diameter less than an inner diameter of the housing to allow the shuttle 3727 to travel in the longitudinal direction in the housing 3701. The shuttle 3727 includes a protuberance that extends upwardly from the body of the shuttle through the slot 3706 to be fixedly received in the recess of the actuator when assembled. The protuberance is positioned closer to the shuttle distal end than the shuttle proximal end. A user can engage the actuator and move the shuttle 3727 proximally and distally along the length of the slot 3706.

The needle clip 1900 can be positioned in either the shuttle 3727 or in the catheter hub. When the needle is retracted from the patient, the sharp needle end is moved proximally past the free ends of the arms 1902, 1903 of the needle safety clip 1900. The needle's sharp end is then secured with the safety clip 1900 as described herein.

Housing 3701 can have an elongate slot to provide visual access into the interior of the housing 3701. The internal components, e.g., the actuator assembly internal parts, the catheter, the needle, etc., can be viewed through the slot. The slot also reduces weight and provides a contact portion for the user's hand to grip and guide the housing.

The needle 3702 has a distal end to insert into a patient and a proximal end that is fixed to a base. The base can be shaped to match the interior of the housing 3701 to allow the needle 103 to travel in the housing and have features as described above. Alternatively, the needle assembly 3701 is fixed to the housing and does not move. The beveled part of the needle end is fixed relative to the housing so that the beveled tip is at the same location. That is, the needle (and other components) does not rotate within the housing interior.

In an example, the needle safety clip 1900 may move exit the distal end of the catheter inserter or a guidewire inserter. For example with reference to FIGS. 37 and 38, the user holds the housing 3701 in one hand with a digit, e.g., index finger or thumb, at the slide or actuator connected to the shuttle. The needle 103 is inserted into the vasculature of a patient. The user engages the slide and moves the slide forward along the slot 3706. The shuttle 3727 engages the catheter assembly and moves the catheter out of the distal end 3702 over the needle 103. In some examples, the catheter is longer than the travel length of the actuator assembly. The user pulls the slide back toward the proximal end. The shuttle disengages from the catheter assembly and the catheter assembly stays in this intermediate position. When the actuator assembly is proximal, it reengages the catheter assembly. The user now slides the actuator assembly forward toward the distal end. The actuator assembly now moves the catheter assembly out the distal end and disengages from the catheter assembly. The housing and needle assembly are retracted proximally with the catheter assembly remaining with the patient. The needle 103 has its sharp end enclosed by the needle clip 1900 when the needle-sharp end retracts through the needle safety clip 1900 to a safety position.

The needle safety clip, in some embodiments, is formed from a unitary body that has a resiliency to be deformed elastically when a needle extends through the clip. The clip thus stores energy. When the needle-sharp end is retracted into the clip, the energy, e.g., the energy in at least one of the arms 1902, 1903, is released and the clip moves to a safety position covering the sharp end of the needle. The clip in its safety position returns to its original size and shape. The clip now resists deformation while allowing a medical device that is smaller than the needle, e.g., a guidewire, to extend through the clip.

Needle safety devices are used to cover the needle tip after use, and can be passive or active. Active devices need to be activated by the user (e.g. by folding a plastic sheath over the needle), whereas passive devices do not require user activation (i.e. the needle safety device is automatically deployed without user intervention). In passive needle safety clips, the needle tip is withdrawn from the catheter hub; the safety clip is deployed to cover the tip of the needle. Examples described herein allow the clip to deploy correctly if a device (e.g., a guidewire) is present and extends past the end of the needle tip. The presently described clip has a unitary body as opposed to a more complicated multiple body needle safety system. Multi-body safety systems are more complicated safety mechanisms that can also interfere with normal use of the medical device (e.g., they may generate excessive friction during catheter advancement over the needle, or require excessive force when removing the needle safety mechanism from the catheter hub). Thus, there is a need for a one-piece, passive needle safety device that functions when a medical device (e.g., a guidewire) is present and extending past the needle tip, and does not interfere with normal device function when compared to a similar device without needle safety.

The safety clip as described herein may be used with various medical device, e.g., Catheter Insertion System as described in PCT Patent Application No. PCT/US16/30026, filed 29 Apr. 2016, titled Catheter Insertion System and Method, which is hereby incorporated by reference for any purpose.

The invention claimed is:

1. A needle safety clip assembly, comprising:
   a housing having a proximal end, a distal end, a transverse upper wall portion, a transverse web portion axially spaced from the transverse wall portion, and an aperture axially between the transverse upper wall portion and the transverse web portion; and
   a needle safety clip engaging the proximal end to fix the needle safety clip on the housing, the needle safety clip including a first section having a hook portion that extends about the transverse upper wall portion to retain at least a portion of the transverse upper wall portion within the hook portion, the hook portion including a terminal end that terminates within the aperture, the terminal end terminating adjacent the transverse upper wall portion, the needle safety clip further including a second section distal from the first section, which at a use position is pressed against a needle and at a safety position with the second section securing a sharp end of the needle within the housing,
   wherein the second section includes a slot to receive a guidewire therethrough in the safety position with the sharp end of the needle being secured, wherein the second section forms a closed end portion at a first end of the slot and an open portion at a second end of the slot, the open portion having a width that is less than the diameter of the needle, wherein the second section is configured to flex outside of the housing in the use position,
   wherein the transverse web portion includes a contact surface that forms a stop for the second section of the needle safety clip.

2. The needle safety clip assembly according to claim 1, wherein the second section flexes to allow the needle to pass through the housing and with the needle retracted past a distal end of the second section.

3. The needle safety clip assembly according to claim 2, wherein the first section wraps around the proximal end of the housing to secure the needle safety clip to the housing.

4. The needle safety clip assembly according to claim 1, wherein the first section engages a proximal transverse end portion of the housing to secure the needle safety clip to the housing.

5. The needle safety clip assembly according to claim 1, wherein the first section includes at least one pair of parallel walls to form an inverted U-shape therebetween.

6. The needle safety clip assembly according to claim 1, wherein the housing includes at least one shelf and wherein the needle safety clip includes at least one wing disposed on the at least one shelf.

7. The needle safety clip assembly according to claim 1, wherein the slot inhibits passage of the needle therethrough in the safety position.

8. The needle safety clip assembly according to claim 1, wherein a longitudinally-extending portion of the first section extends parallel to the needle.

9. The needle safety clip assembly according to claim 1, wherein a longitudinally-extending portion of the second section extends parallel to the needle.

10. The needle safety clip assembly according to claim 1, wherein the housing includes a lower transverse web that extends between the first section and the needle.

11. A needle safety clip assembly, comprising:
    a housing having a proximal end, a distal end, and an aperture; and
    a needle safety clip extending around the proximal end to fix the needle safety clip on the housing, the needle safety clip including a first section and a second section distal from the first section, wherein at a use position, the second section is pressed against a needle, and at a safety position, the second section secures a sharp end within the housing;
    wherein the first section includes a transverse proximal wall portion that extends along the proximal end of the housing, and a transverse terminal free end portion axially between the transverse proximal wall portion and the second section and terminating within the aperture, and wherein the second section includes a slot to receive a guidewire therethrough in the safety position with the sharp end being secured.

12. A needle safety clip assembly, comprising:

a housing having a proximal end that includes a rear web portion having a transverse upper wall portion, a distal end, and an aperture axially between the rear web portion and the distal end;

a needle safety clip having a first portion that wraps around the rear web portion to fix the needle safety clip on the housing, the first portion having a rear wall for extending upwardly outside of the housing at a first axial side of the rear web portion, an upper transverse wall that extends from the rear wall to be above the transverse upper wall portion, and a retaining leg that extends from the upper transverse wall to extend into and terminate within the aperture, the retaining leg terminates adjacent the transverse upper wall portion and retains the rear web portion between the retaining leg and the rear wall, and a second section distal from the first portion, which at a use position is pressed against a needle and at a safety position with tea distal end of the second section securing a sharp end within the housing, the second section including a slot to receive a guidewire therethrough in the safety position with the sharp end being secured.

13. The needle safety clip assembly according to claim 12, wherein the rear web portion is an upper rear web portion, the housing further including a lower rear web portion having a transverse lower wall portion, the needle safety clip including a lower transverse wall that extends from the rear wall to be below the transverse lower wall portion.

* * * * *